US007946992B2

(12) United States Patent
Umemura et al.

(10) Patent No.: US 7,946,992 B2
(45) Date of Patent: May 24, 2011

(54) VELOCITY MEASURING METHOD AND VELOCITY MEASURING DEVICE USING THE SAME

(75) Inventors: Shinichiro Umemura, Sendai (JP); Takashi Azuma, Kodaira (JP); Tetsuya Hayashi, Kashiwa (JP); Naoyuki Murayama, Kashiwa (JP)

(73) Assignee: Hitachi Medical Corporation, Tokyo (JP)

(*) Notice: Subject to any disclaimer, the term of this patent is extended or adjusted under 35 U.S.C. 154(b) by 147 days.

(21) Appl. No.: 11/915,625

(22) PCT Filed: Jan. 6, 2006

(86) PCT No.: PCT/JP2006/300081
§ 371 (c)(1),
(2), (4) Date: Mar. 19, 2009

(87) PCT Pub. No.: WO2006/126303
PCT Pub. Date: Nov. 30, 2006

(65) Prior Publication Data
US 2009/0177091 A1    Jul. 9, 2009

(30) Foreign Application Priority Data

May 27, 2005   (JP) .................................. 2005-154844

(51) Int. Cl.
*A61B 8/00* (2006.01)
(52) U.S. Cl. ........ 600/455; 600/453; 600/454; 600/456; 600/457; 600/437; 600/407
(58) Field of Classification Search .................. 600/437, 600/441–445, 453–457; 367/135, 11, 7
See application file for complete search history.

(56) References Cited

U.S. PATENT DOCUMENTS
4,884,448 A   12/1989   Ogawa et al.
5,228,009 A   7/1993    Forestieri et al.

OTHER PUBLICATIONS

Umemura et al, "Clutter-Free Doppler Detection of Signed Velocity based on Legendre Seires Expansion", 2004 IEEE International Ultrasonics Symposium, Ferroelectrics and Frequency Control Joint 50th Anniversary Conference, pp. 588-591.

(Continued)

*Primary Examiner* — Tse Chen
*Assistant Examiner* — Joel F Brutus
(74) *Attorney, Agent, or Firm* — Antonelli, Terry, Stout & Kraus, LLP.

(57) ABSTRACT

The present invention is to provide a velocity measuring method and a velocity measuring device for carrying out the method. The velocity measuring method includes: a step (S4) for expanding N time series signals by using 0-th to (N−1)-th degree discrete Legendre function as a base; a step (S5) for calculating 2n-th degree complex expansion coefficient by multiplying a linear combination of a (2n−1)-th degree expansion coefficient and a (2n+1)-th degree expansion coefficient by an imaginary unit and then linearly combining the result and a 2n-th degree expansion coefficient, and calculating a (2n+1)-th degree complex expansion coefficient by multiplying the (2n+1)-th degree expansion coefficient by an imaginary unit and then linearly combining the result, the 2n-th degree expansion coefficient and a (2n+2)-th degree expansion coefficient; a degree decision step (S4) for determining the degree m of a coefficient having the maximum absolute value among the complex expansion coefficients; and a step (S8) for calculating a signed velocity signal concerning a moving reflection object from a ratio of square sums of the expansion coefficients or complex expansion coefficients corresponding to the degree m.

9 Claims, 37 Drawing Sheets

OTHER PUBLICATIONS

Hans Torp, "Clutter Rejection Filters in Color Flow Imaging: A Theoretical Approach", IEEE Transactions on Ultrasonics, Ferroelectrics and Frequency Control, vol. 44 No. 2, Marcy 1997, pp. 417-424.

Steiner Bjaerum, "Optimal Adaptive Clutter Filtering in Color Flow Imaging", 1997 IEEE Ultrasonics Symposium, pp. 1223-1226.

"On the Performance of Regression and Step-Initialized IIR Clutter Filters for Color Doppler Systems in Diagnostic Medical Ultrasound", Kadi et al, IEEE Transactions on Ultrasonics, Ferroelectrics, and Frequency Control, vol. 423, No. 5, Sep. 1995, pp. 927-937.

"On the Performance of Regression and Step-Initialized IIR Clutter Filters for Color Doppler Systems in Diagnostic Medical Ultrasound", Kadi et al, IEEE Transactions on Ultrasonics, Ferroelectrics, and Frequency Control, vol. 42, No. 5, Sep. 1995, pp. 927-937.

FIG..28

PHASE ROTATION VELOCITY CORRESPONDING TO BLOOD
FLOW VELOCITY / SAMPLING ANGULAR FREQUENCY

VELOCITY MEASURING METHOD AND VELOCITY MEASURING DEVICE USING THE SAME

FIELD OF THE INVENTION

The present invention relates to a velocity measuring method using a reflected pulse wave, and a velocity measuring device using the method.

RELATED ART

In a pulse Doppler velocimeter, a plurality of pulse waves are transmitted to a moving reflection object, and a plurality of received echo signals as shown in FIG. 1 are analyzed. In other words, a plurality of signals respectively received at a plurality observation times each equal to a fixed elapsed time from the time when the pulse waves are transmitted, namely a plurality of time series signals arranged in order of transmission time, are analyzed to obtain the information about the moving reflection object such as the velocity. The most typical signal processing method is to orthogonally detect the received signals and analyze the detected signals as complex time series signals. Such a pulse Doppler velocimeter is widely used as an ultrasonic diagnostic apparatus for detecting and drawing the blood flow in a living body, as a weather radar for drawing nimbuses and the like, or as an aviation radar for detecting flying objects.

In the case where there is only one reflection object, the moving velocity of the reflection object toward a transmitter/receiver can be obtained by the following equation from a phase rotation velocity $\Delta\Phi/\Delta t$ of the time series signals, namely from a signed angular frequency.

$$v = \lambda \Delta\Phi/\Delta t/2 \qquad (1)$$

Where the $\lambda$ represents a wavelength, the $\Delta t$ represents an interval at which the pulse transmission is performed, and the $\Delta\Phi$ represents a phase rotation angle. The moving velocity has a positive sign when the reflection object moves toward, and the moving velocity has a negative sign when the reflection object moves away.

However, among the actually received echo signals, the echo signals reflected from the stationary reflection object (so called the "clutter signals") are usually stronger than the observed echo signals reflected from the moving reflection object by several figures or more. Further, instead of being entirely stationary with respect to the time axis, the echo signals reflected from the stationary reflection object are actually drifting due to the fluctuation of the medium in the transmission path or due to, in the case of an ultrasonic diagnostic apparatus, the slow movement of stationary organs other than the blood flow. Thus, the frequency components of the echo signals reflected from the stationary reflection object include not only the direct-current component whose phase rotation velocity is zero, but also low frequency component whose phase rotation velocity is not zero.

Thus, the velocity of the moving reflection object can not be detected simply by applying the equation (1) to the time series signals. To solve this problem, in an actual pulse Doppler velocimeter, the velocity is detected or analyzed after performing a signal process of so called "MTI (Moving Target Indicator) process" in which the echo signals reflected from the stationary reflection object are restricted and the echo signals reflected from the moving reflection object are relatively strengthen.

The most well known MTI process is the process performed by a conventional low frequency cutoff filter expressed by a convolution in the time domain. Such a process has the following two defects.

1) In the case where a low frequency cutoff filter in which N1 time series data points are input is used, the number of the time series data points input into the velocity detection/analysis processing section of a latter stage will decrease by (N1−1).

2) It is difficult to obtain a filter having a steep cutoff characteristic.

A steep cutoff characteristic which can remove the drift components of the stationary reflection object while retaining echo signals reflected from the moving reflection object is necessary for a pulse Doppler velocimeter. Therefore, the aforesaid second defect is particularly a problem for a pulse Doppler velocimeter. Further, the problem of the aforesaid second defect, namely the problem that the number of the data points decreases when performing velocity detection/analysis to the N time series signals obtained by performing N transmitting/receiving operations, means that the number of the data points possible to be actually used for performing velocity detection/analysis calculation will be reduced to (N−N1+1) points. This will be undesirable for application where a real time characteristic is important, such as a diagnostic ultrasonic blood flow drawing device.

As a process for solving this problem, a polynomial regression filter described in Nonpatent Literature 1 is suggested. In this process, a least square fitting method is performed to the time series signals in order of expression of degree 0 (which is a constant), expression of degree 1, . . . , expression of degree M, and the fitted components are subtracted so that the drift components contained in the original time series signals are removed. This process is expressed as multiplying the N points of input time series signals by a square matrix N×N. Accordingly: 1) As output signals, N points of time series signals can be obtained, which is the number identical to the points of input time series signals, so that number of the data points does not decrease. 2) Although the low frequency cutoff characteristic of this process depends on value of the maximum degree M to be fitted, the low frequency cutoff characteristic is far steeper than the cutoff characteristic of the low frequency cutoff filter having the same cutoff frequency.

[Nonpatent Literature 1] IEEE Transactions on Ultrasonics, Ferroelectrics, and Frequency Control, Vol. 42, No. 5, September 1995, pp 927-937.

DISCLOSURE OF THE INVENTION

However, in a latter stage of the process using the polynomial regression filter, when using the equation $v=\lambda\Delta\Phi/\Delta t/2$ to detect/analyze the velocity of the moving object, a velocity calculation error in the vicinity of cutoff frequency will be larger than that caused by using the low frequency cutoff filter. For this reason, the steep cutoff characteristic of the polynomial regression filter can not be fully used.

An object of the present invention is to provide a velocity measuring method capable of distinguishing between a reflected signal of a stationary reflection object and a reflected signal of a moving reflection object and reducing the measuring error as well as to provide a velocity measuring device using the velocity measuring method.

The present invention expands N time series signals by using 0-th to (N−1)-th degree discrete Legendre function as a base, and uses expansion coefficients to calculate the velocity, in which the N time series signals are formed by arranging echo signals of N pulse waves, which are transmitted toward the velocity measuring object at a predetermined time interval, in order of the transmission time. Particularly, the present invention calculates a 2n-th degree complex expansion coefficient by multiplying a linear combination of a (2n−1)-th degree expansion coefficient and a (2n+1)-th degree expansion coefficient by an imaginary unit and then linearly combining the result and a 2n-th degree expansion coefficient, and calculates a (2n+1)-th degree complex expansion coefficient by multiplying the (2n+1)-th degree expansion coefficient by an imaginary unit and then linearly combining the result, the 2n-th degree expansion coefficient and a (2n+2)-th degree expansion coefficient wherein the degree of the expansion coefficients is 1 or over and (N−1) or below; determines the degree m of a coefficient having the maximum absolute value among the complex expansion coefficients; and calculates a signed velocity signal concerning the moving reflection object from a ratio of square sums of the expansion coefficients or complex expansion coefficients corresponding to the degree m.

The echo signals having a phase rotation velocity (an angular frequency) of $\Delta\Phi/\Delta t$ are obtained from a moving reflection object, to which the pulse waves are transmitted, and clutter signals having low-frequency components are obtained from a stationary reflection object which drifts. The strength of the clutter signals is incomparably greater than that of the echo signals. The echo signal of the moving reflection object and the low-frequency of the stationary reflection object are distinguished from each other by expanding the echo signal using the discrete Legendre function as base and relating the horizontal axis of the respective expansion coefficients to the phase rotation velocity (the angular frequency), the discrete Legendre function having a character that is: in the vicinity of the frequency origin, the higher the degree is, the more rapidly the value is converged to zero. In other words, the reflected signal of the stationary reflection object and the reflected signal of the moving reflection object can be distinguished from each other.

According to the present invention, the reflected signal of the stationary reflection object and the reflected signal of the moving reflection object can be distinguished from each other, and the measuring error can be reduced.

BEST MODE FOR CARRYING OUT THE INVENTION (Principle of Filter)

The following description is directed to a case where the velocity analysis is performed to a plurality of signals respectively received at a plurality observation times each equal to a fixed elapsed time from the time when the respective pulse waves are transmitted, based on N discrete time series signals arranged in order of the transmission time. The typical time series complex signals used to perform a pulse Doppler velocity analysis can be obtained by: obtaining a pair of signals by multiplying each of the received echo signals by two carrier frequency signals different by 90° in phase, linearly combining the pair of signals with an imaginary unit as a coefficient to obtain a complex signal, arranging the parts having the same time phase (with the respective pulse transmission times as reference) of each of the complex signals in order of the transmission time.

The usual method for analyzing the frequency or phase of the discrete time series signals is performing a discrete Fourier expansion, Specifically, expanding the time series signals arranged in order of n=1, 2, . . . , N by using a complex sine wave system:

$$Cs(n, k) = \cos[k\pi(2n-N-1)/N] + j\sin[k\pi(2n-N-1)/N] \quad (2)$$

where the exponent (which represents frequency) k=−N/2, . . . , 0, . . . , N/2, j is an imaginary unit.

The negative k corresponds to a velocity at which the reflection object moves away while the positive k corresponds to a velocity at which the reflection object moves closer. Since the k=±N/2 represents a Nyquist limit without distinction of positive or negative, there are N independent complex sine wave functions among the (N+1) complex sine wave functions represented by the equation (2), and the N independent complex sine wave functions form a system of orthogonal functions.

Figure 2:
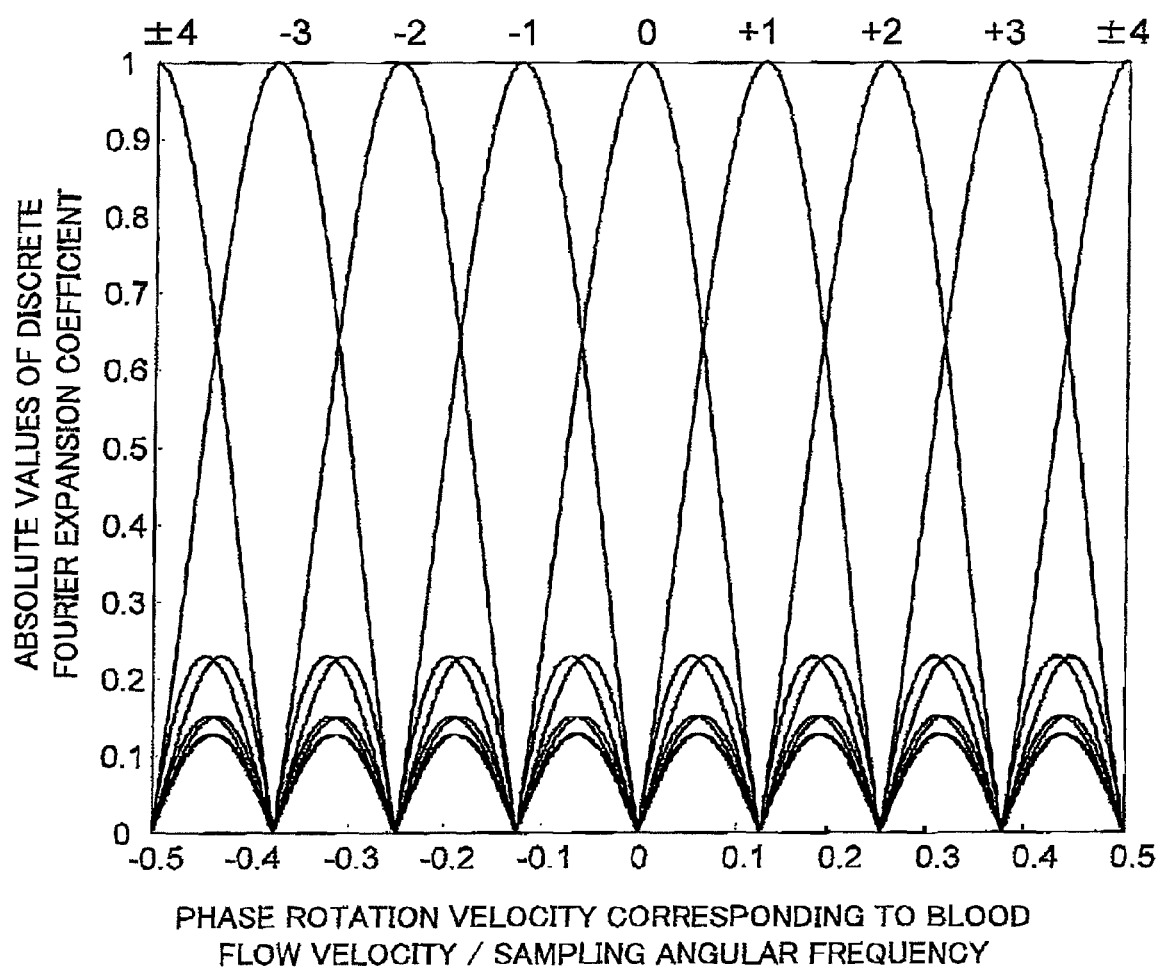
FIG. 2 shows absolute values of a discrete Fourier expansion coefficient as functions of a signed frequency corresponding to the velocity.

In a case where there is only one reflection object moving within the range of the Nyquist limit at a fixed velocity, the discrete Fourier expansion coefficients obtained by performing the above expansion are calculated, and the absolute values thereof (in the case where N=8) are plotted in FIG. 2 as functions of the velocity. The horizontal axis represents a phase rotation velocity (which corresponds to the moving velocity), and the unit of the horizontal axis is 2π times pulse repetition frequency of the pulse transmission. FIG. 2 shows eight functions, each representing an expansion coefficient, overlapped to each other and therefore FIG. 2 is very difficult to view. To be easy to view, FIG. 2 is divided into FIG. 3 and FIG. 4, each showing four functions respectively indicated by different lines which can be easily distinguished from each other.

To a moving velocity whose phase is rotated by integer number of rotations over a time interval which equals to N times transmission interval, there is only one expansion coefficient which is not zero, the other expansion coefficients are all zero, so that the velocity analysis can be perfectly performed. However, to a general moving velocity whose phase is not rotated by integer number of rotations, the absolute value of the expansion coefficient will be about 1/10 of peak value even at a moving velocity far away from the moving velocity corresponding to the peak in the horizontal axis. This means that the velocity analyzer has a remote crosstalk of about −20 dB. When the clutter signals, which have amplitudes incomparably greater than those of the moving reflection object echoes to be detected and analyzed, drift, it will be difficult to distinguish between the echo signals reflected from the clutter and the echo signals reflected from the moving reflection object, and that will be a serious problem.

This problem can not be basically solved, though it can be considerably restricted by weighing the N time series signals with a window function such as a Hanning function which gently rises and falls. Further, this method has an undesirable effect which causes great reduction of the number of the time series signals, and therefore is particularly unsuitable to a case where the number of the time series signal is originally small.

Figure 5:
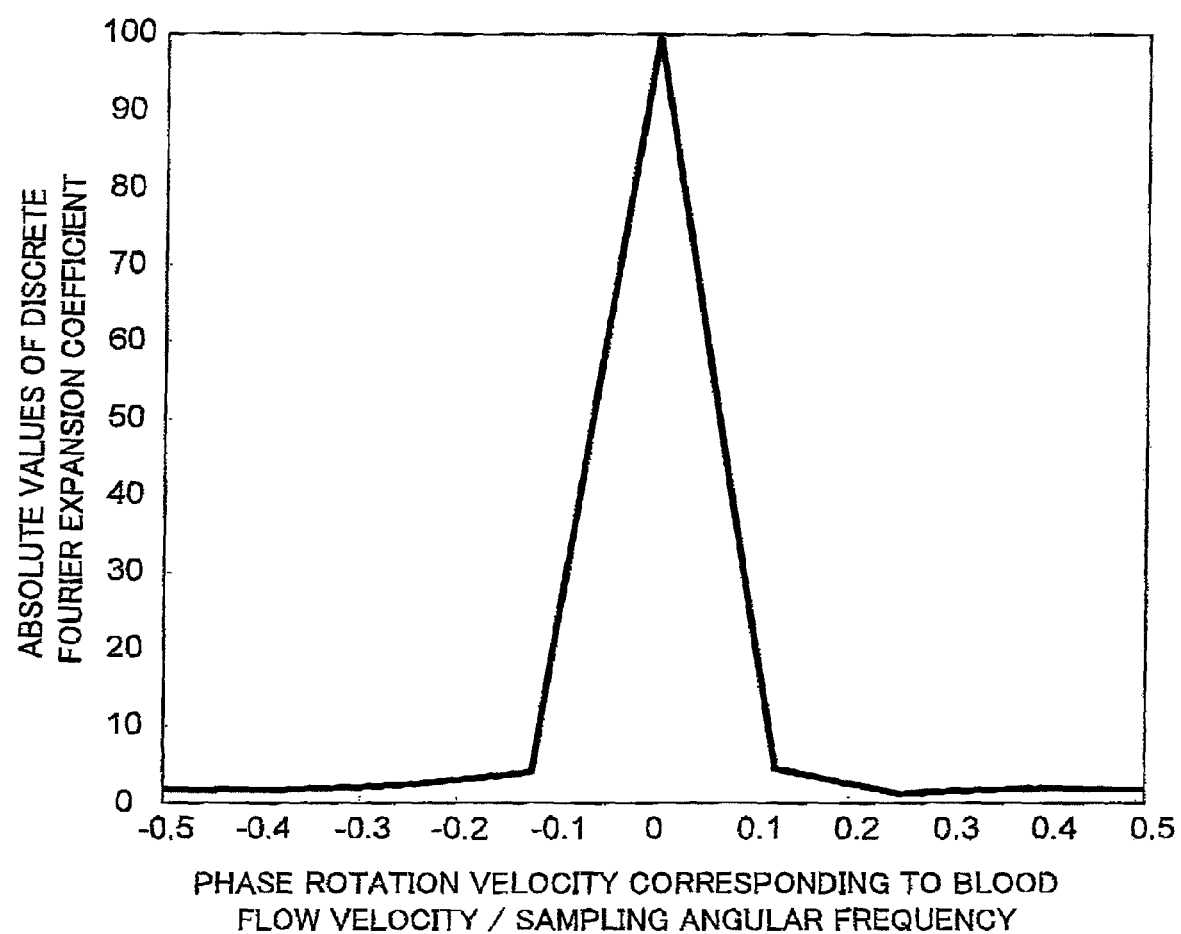
FIG. 5 shows an example of a velocity spectrum coefficient obtained by performing velocity analysis using the discrete Fourier expansion.

The following discussion is based on an example in which a moving reflection object to be detected and analyzed moves at a fixed velocity equal to ⅔ of the Nyquist limit, while a clutter signal drifts at a velocity equal to 1/100 of the Nyquist limit, the clutter signal having an amplitude that is 1,000 times as high as that of the moving reflection object. FIG. 5 shows a velocity spectrum output by the velocity analyzer in this example. The spectrum of the moving reflection object to be detected and analyzed is covered and concealed by crosstalk components from a clutter signal which reaches to a peak value around the velocity of zero, and therefore can not be detected from the output spectrum. This is the most essential reason why a MTI filter for cutting off the clutter signal is indispensable.

Figure 6:
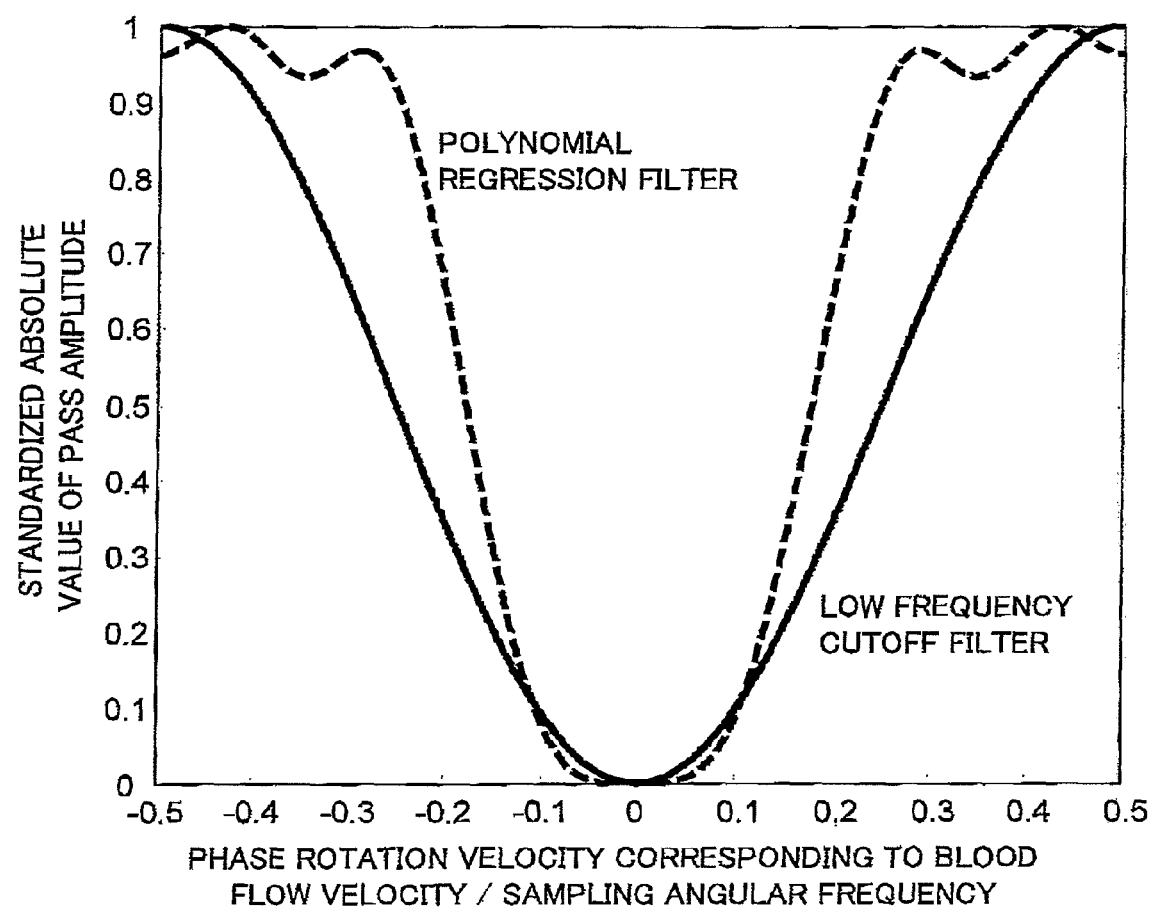
FIG. 6 shows a typical example of a pass amplitude characteristic of a conventional low frequency cutoff MTI filter and a typical example of a pass amplitude characteristic of a polynomial regression filter.
Figure 7:
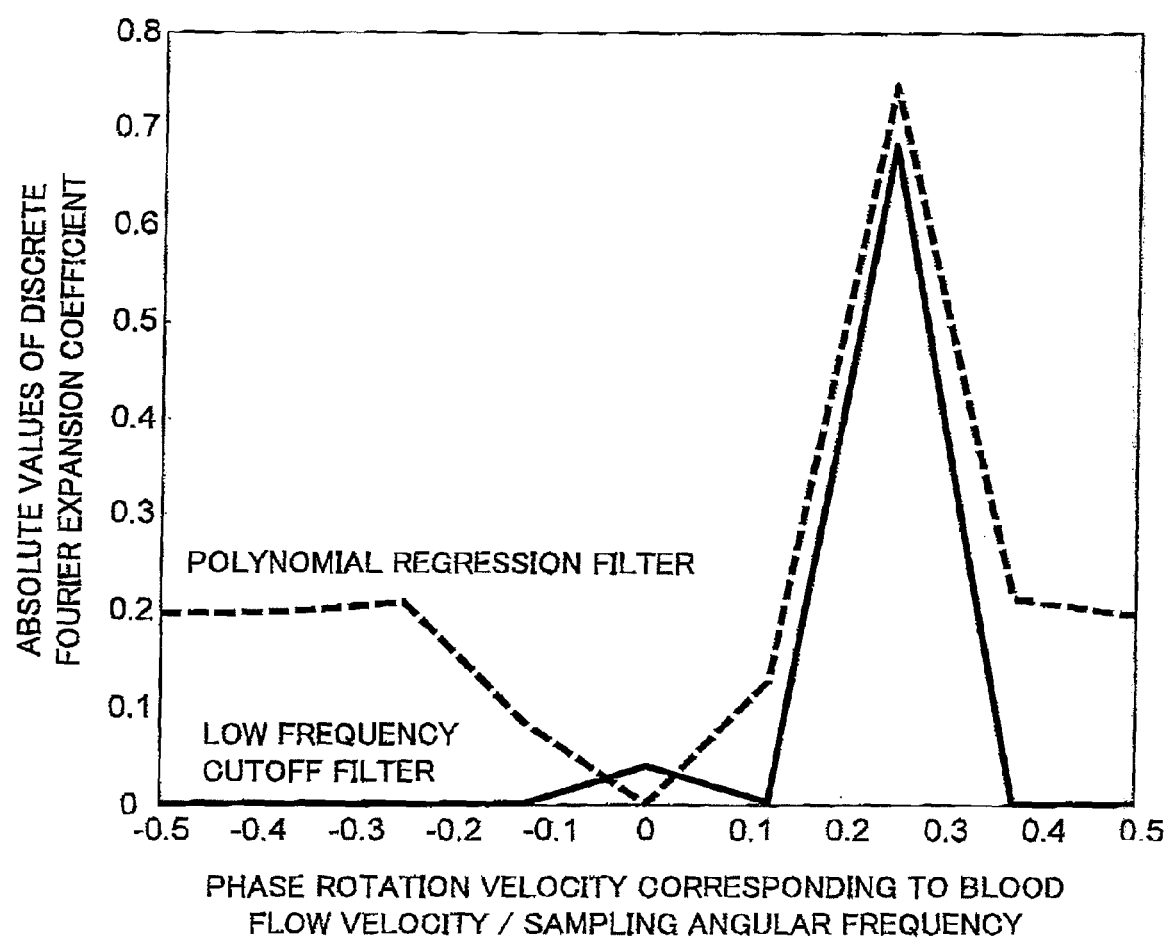
FIG. 7 shows an example of a velocity spectrum coefficient obtained by performing velocity analysis using the discrete Fourier expansion after passing through a conventional low frequency cutoff MTI filter and an example of a velocity spectrum coefficient obtained by performing velocity analysis using the discrete Fourier expansion after passing through a polynomial regression filter.

In FIG. 6, the continuous line represents a typical example of a pass amplitude characteristic of the conventional low frequency cutoff filter expressed by a convolution in a time domain, the low frequency cutoff filter being the most well known MTI process. If time series signals S1(n1) arranged in order of n1=1, . . . , (N+M−1) are input into such a filter, then time series signals S0(n0) arranged in order of n0=1, . . . , N can be obtained as an output.

$$S0(n0) = \Sigma F(m)S1(n0+m-1) \quad (3)$$

where Σ represent a sum of m=1, . . . , M. In FIG. 6, the continuous line represents a simplest case of a pass amplitude characteristic of the low frequency cutoff filter in which M=3, F(1)=−1, F(2)=2, and F(3)=−1. If the velocity analysis as performed in FIG. 5 is performed to the input signal as input in FIG. 5 after passing through the low frequency cutoff filter, the result will be the continuous line of FIG. 7. Due to the effect of the low frequency cutoff filter, the amplitude of the clutter signal is restricted to approximately 1/2000, therefore the spectrum of the moving reflection object, which reaches the peak at a velocity that is 0.3 to 0.4 times the Nyquist limit, can be observed.

The broken line in FIG. 6 represents a typical example of the pass amplitude characteristic of a polynomial regression filter as a MTI filter serving the same purpose. In this example, expressions of degree 0 to degree 3 are fitted and subtracted. The filter has a low frequency cutoff characteristic steeper than that of the convolution filter. Further, if the velocity analysis as performed in FIG. 5 is performed to the input signal as input in FIG. 5 after passing through the low frequency cutoff filter, the result will be the broken line of FIG. 7. Owing to the steepness of the low frequency cutoff characteristic, the clutter signals are completely restricted. The specific steep low frequency cutoff characteristic of the polynomial regression filter can be perceived via the following description.

Narrowly-defined Legendre polynomial in a continuous coordinate system can be found in *Iwanami Mathematic Formula III, Special Function*, pp. 82-85, and expressions up to degree 8 is listed as follows.

$$P_0(x) = 1$$
$$P_1(x) = x$$
$$= \cos\theta$$
$$P_2(x) = (1/2)(3x^2 - 1)$$
$$= (1/4)(3\cos2\theta + 1)$$
$$P_3(x) = (1/2)(5x^3 - 3x)$$
$$= (1/8)(5\cos3\theta + 3\cos\theta)$$
$$P_4(x) = (1/8)(35x^4 - 30x^2 + 3)$$
$$= (1/64)(35\cos4\theta + 20\cos2\theta + 9)$$
$$P_5(x) = (1/8)(63x^5 - 70x^3 + 15x)$$
$$= (1/128)(63\cos5\theta + 35\cos3\theta + 30\cos\theta)$$
$$P_6(x) = (1/16)(231x^6 - 315x^4 + 105x^2 - 5)$$
$$= (1/512)(231\cos6\theta + 126\cos4\theta + 105\cos2\theta + 50)$$
$$P_7(x) = (1/16)(429x^7 - 639x^5 + 315x^3 - 35x)$$
$$= (1/2^{10})(429\cos7\theta + 231\cos5\theta + 189\cos3\theta + 175\cos\theta)$$
$$P_8(x) = (1/128)(6435x^8 - 12012x^6 + 6930x^4 - 1260x^2 + 35)$$
$$= (1/2^{14})(6435\cos8\theta + 3432\cos6\theta + 2772\cos4\theta + 2520\cos2\theta + 1225)$$

In order to be able to be also used in a discrete coordinate system, the above expressions are generalized so that an even (2n) degree Legendre polynomial can be defied as an even function which is orthogonal to all Legendre polynomials having degree lower than 2n and whose highest degree is 2n, and that an odd (2n+1) degree Legendre polynomial can be defined as an odd function which is orthogonal to all Legendre polynomials having degree lower than (2n+1) and whose highest degree is (2n+1).

Figure 8:
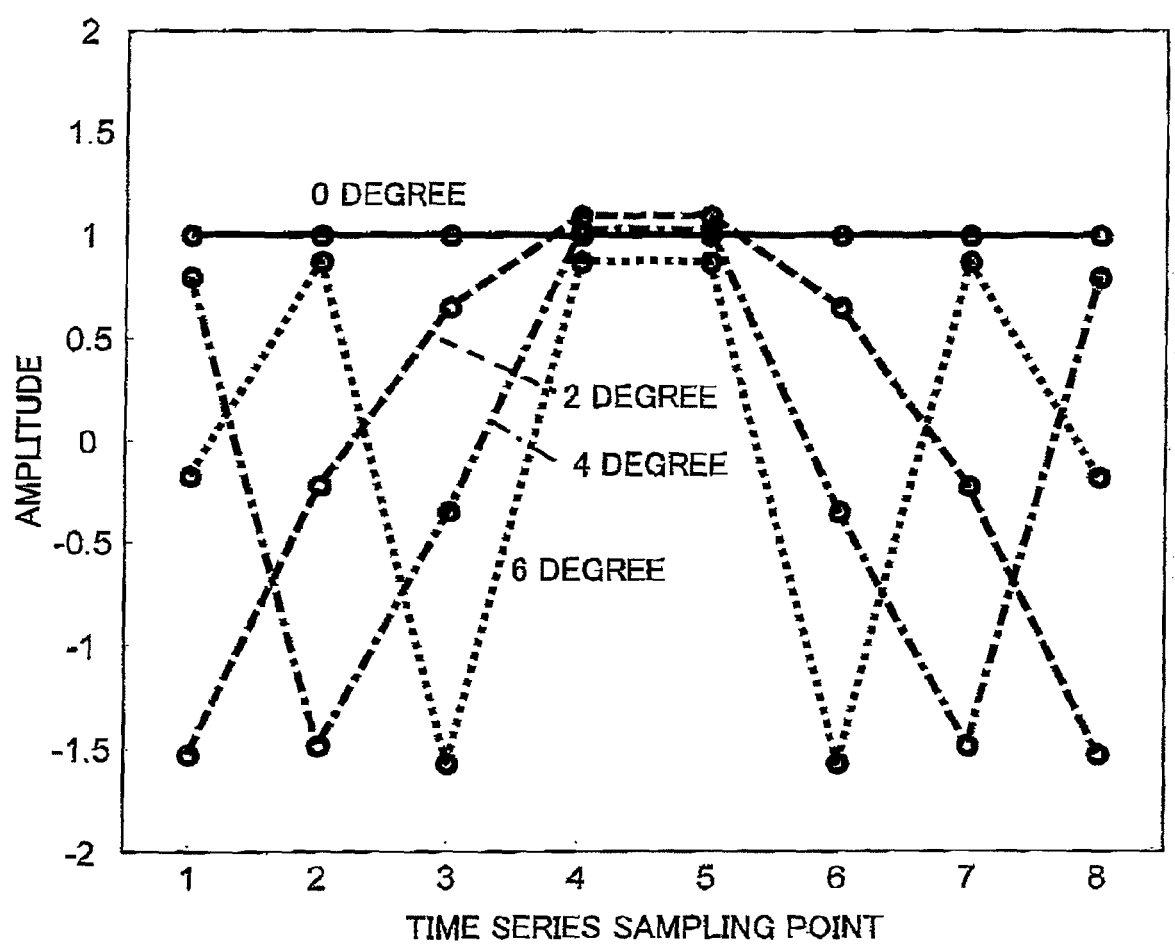
FIG. 8 shows even degree discrete Legendre functions calculated for a row of time series signals of 8 points.
Figure 9:
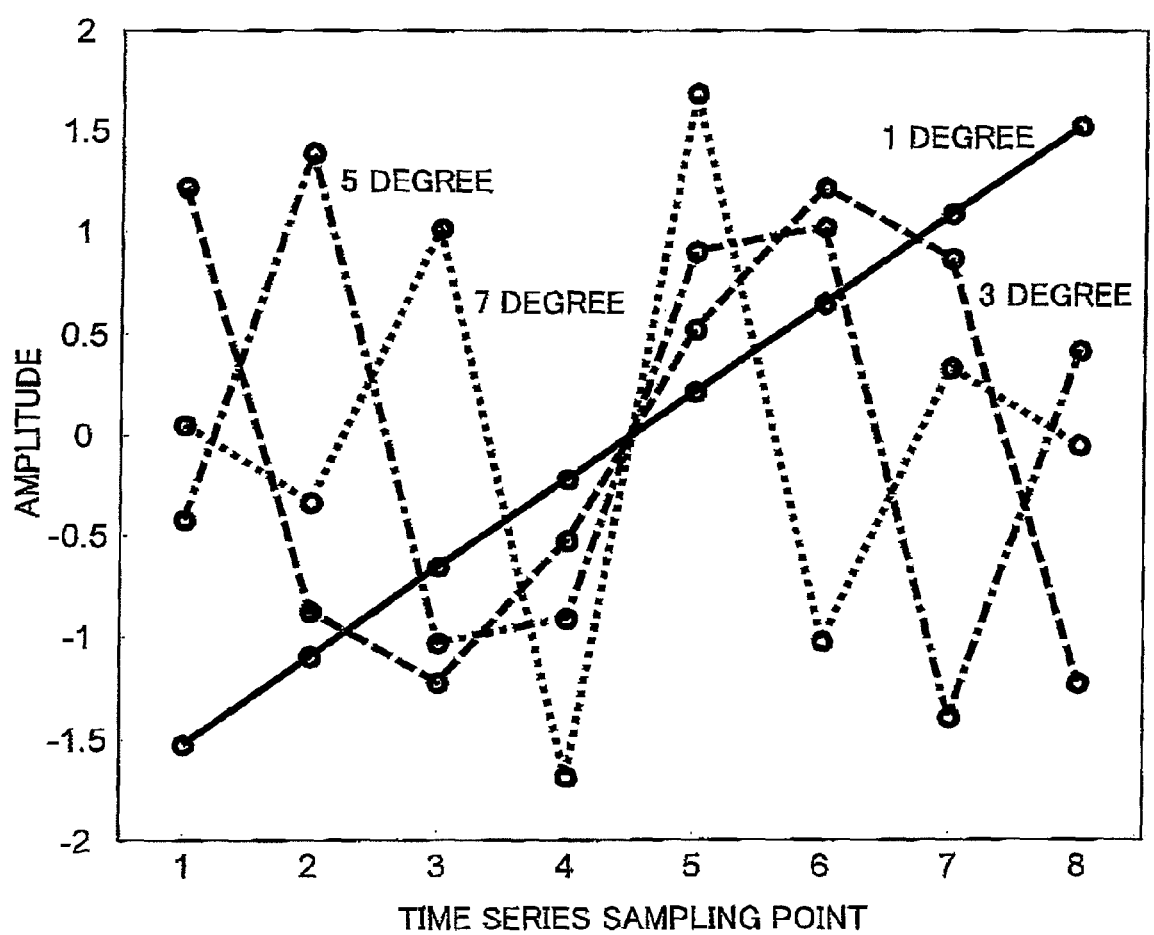
FIG. 9 shows odd degree discrete Legendre functions calculated for the row of time series signals of 8 points.
Figure 10:
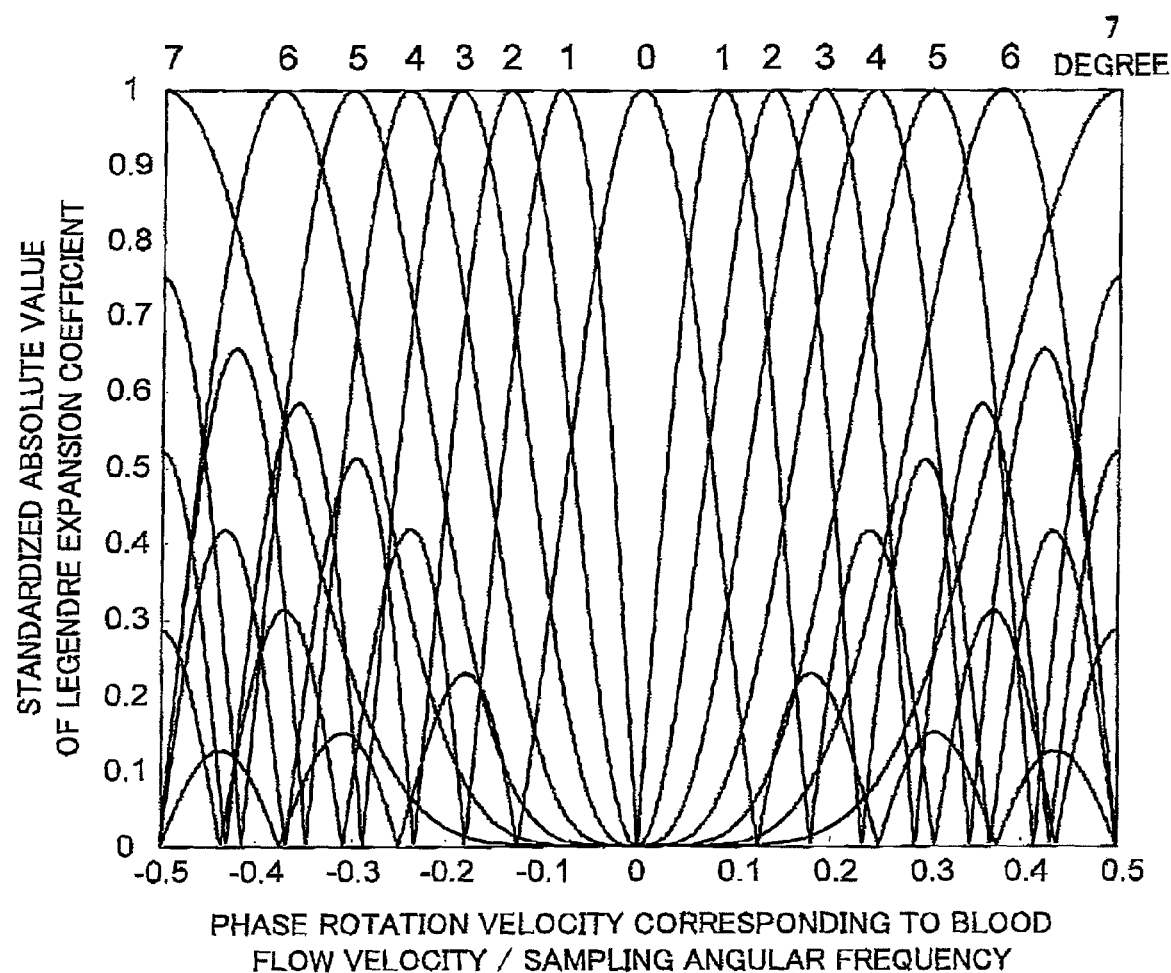
FIG. 10 shows standardized absolute values of the Legendre expansion coefficients as functions of the signed frequency corresponding to the velocity.
Figure 11:
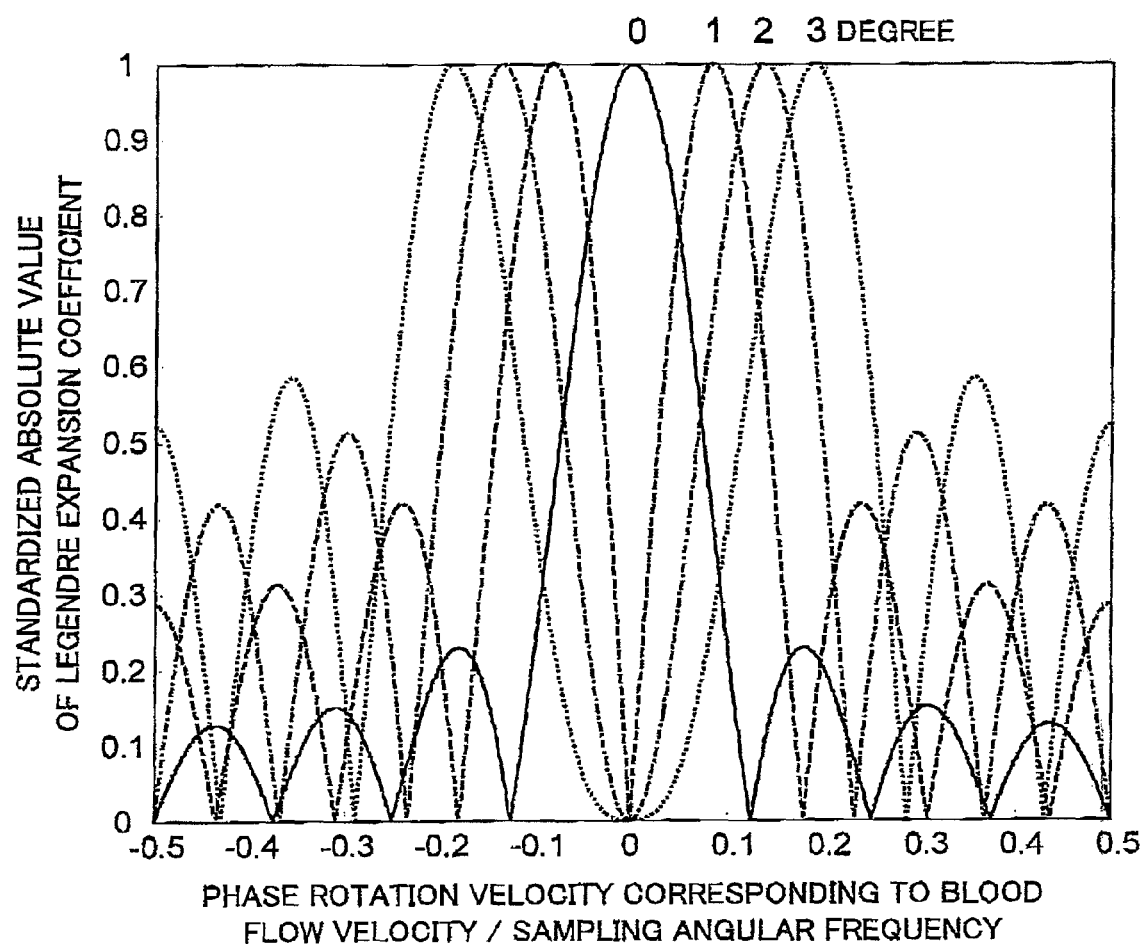
FIG. 11 shows the standardized absolute values of the Legendre expansion coefficients as the functions of the signed frequency corresponding to the velocity.
Figure 12:
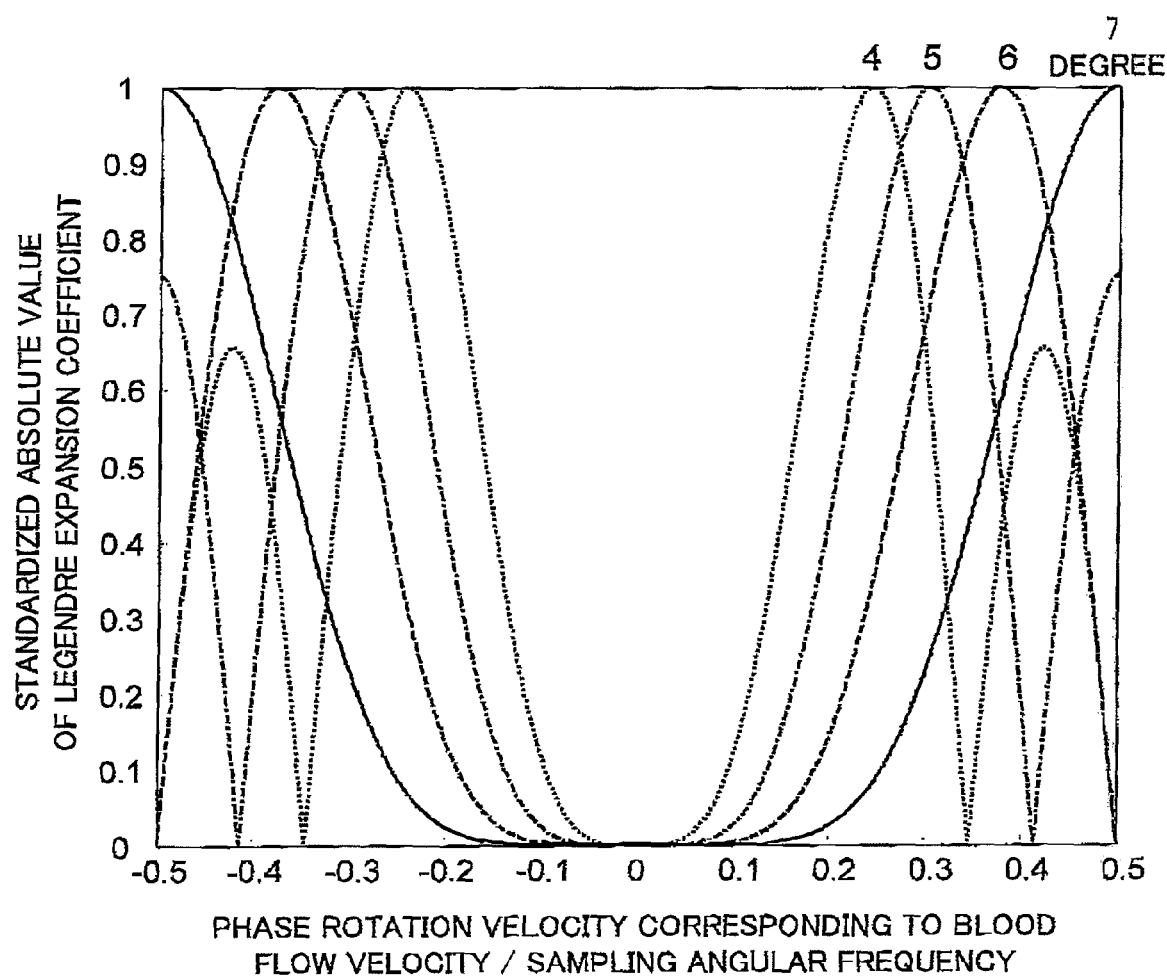
FIG. 12 shows the standardized absolute values of the Legendre expansion coefficients as the functions of the signed frequency corresponding to the velocity.

As an example, 0-th to 7th degree discrete Legendre functions are calculated for a row of time series signals of 8 points, the even degree Legendre functions are shown in FIG. 8, and the odd degree Legendre functions are shown in FIG. 9. The o-th degree and 1st degree are indicated by continuous lines, the 2nd degree and 3rd degree are indicated by broken lines, the 4th degree and 5th degree are indicated by dot and dash lines, and the 6th degree and 7th degree are indicated by dot lines. The amplitudes are standardized so that the RMS (Root Mean Square) of the amplitude equal to 1. The sign is so defined that the sign of the lowest degree term is positive. Namely the sign is so defined that the sign of the constant term is positive in the case of an even degree polynomial and that the sign of the 1st degree term is positive in the case of an odd degree polynomial. The frequency spectrum is plotted in FIG. 10. In FIG. 10, the absolute values of the amplitudes of the frequency components are standardized by the maximum values of the respective Legendre expansion coefficients. FIG. 10 shows eight functions overlapped to each other and therefore FIG. 10 is very difficult to view. To be easy to view, FIG. 10 is divided into FIG. 11 and FIG. 4, each showing four functions respectively plotted by different lines which can be easily distinguished from each other. A(0) and A(7) are indicated by continuous lines, A(1) and A(6) are indicated by broken lines, A(2) and A(5) are indicated by dot and dash lines, and A(3) and A(4) are indicated by dot lines.

Similar to FIGS. 2 to 4, FIGS. 10 to 12 can be viewed as frequency responses to an input complex sine wave. The peaks represent main responses, and the others represent sub represents. Compared to the Fourier expansion system shown in FIGS. 2 to 4, the Legendre function has stronger sub responses on the higher frequency side of the main response but has no sub response on the lower frequency side of the main response. Also, compared to the Fourier expansion system, in the vicinity of the frequency origin, the higher the degree is, the more rapidly the value is converged to zero. Although the analytic proof is omitted, at the frequency origin, 0-th to (m−1)-th degree derivatives of a m degree Legendre function (which is a function of frequency) are all zero.

The aforesaid polynomial regression filter can be considered as a filter which expands the input signals using the discrete Legendre function as a base, removes 0-th to M-th degree components, and treats the (M+1)-th or higher degree components as output signals. Thus, in the vicinity of the frequency origin, the output signals converge into zero at a speed which is proportional to (M+1)-th power of frequency. Due to the above essential characteristic of the Legendre function, the polynomial regression filter has excellent low frequency cutoff characteristic as can be seen from examples indicated by the broken lines in FIGS. 6 and 7. Thus, the method which uses the polynomial regression filter or Legendre function expansion is essentially suitable to the Doppler velocity detection which has to detect the velocity of a moving object being observed and analyze the detected velocity while restrict the effect of the clutter which is an interference component having incomparably greater amplitude in the vicinity of the frequency origin.

It is widely known that the Fourier expansion system, which uses the complex sine wave as a base, can be used to perform signed velocity analysis as shown in FIGS. 2 to 5 and FIG. 7, and such an analysis method is widely used. Although the Legendre expansion system has a character extremely suitable to Doppler velocity detection as discussed above, if it is used as it is, since the responses to the velocities having the same absolute value but different sign are the same as shown in FIGS. 10 to 20, it can be used to perform signed velocity analysis.

However, if an even degree Legendre function and an odd degree Legendre function having degree different from each other by one are linearly combined with an imaginary unit as a coefficient to generate a complex Legendre function, the complex Legendre function can be used to perform the signed velocity analysis. This is because the change of the even degree Legendre function is similar to the change of a cosine wave and the change of the odd degree Legendre function is similar to the change of a sine wave so that by linearly combining the cosine function and the sine function with an imaginary unit as a coefficient, an exponent function (namely a complex sine function) having a phase angle multiplied by j can be obtained, so that a signed velocity can be obtained from the complex Legendre function, just like the case where a signed velocity can be obtained from the increase/decrease of the phase angle.

Specifically, the steps are: expanding a row of time series signals of N points by using 0-th to (N−1)-th degree discrete Legendre function as a base to obtain expansion coefficients of A(0) and A(N−1), calculating a row of complex Legendre coefficients based on the obtained expansion coefficients, and performing the signed velocity analysis according to the relative amplitude of the calculated complex Legendre coefficients.

$$C(\pm(2n-3/2))=A(2n-2)\pm jA(2n-1)$$

where $1 \leq 2n-1 \leq N-1$; n: natural number; double signs in same order.

$$C(\pm(2n-1/2))=A(2n)\pm jA(2n-1) \qquad (4)$$

where $2 \leq 2n \leq N-1$; n: natural number; double signs in same order.

Figure 1:
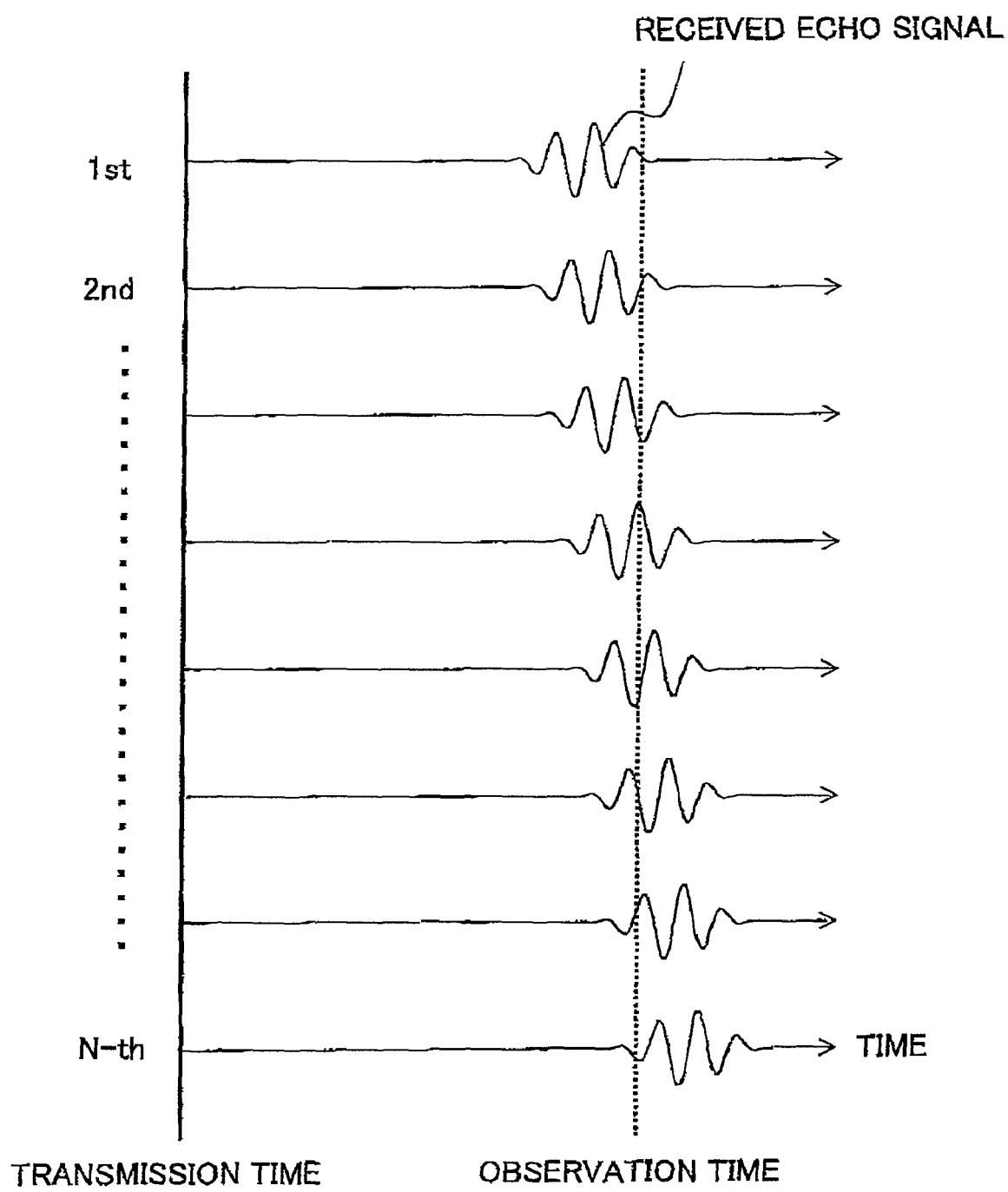
FIG. 1 shows a row of received signals reflected by N pulse transmissions.
Figure 13:
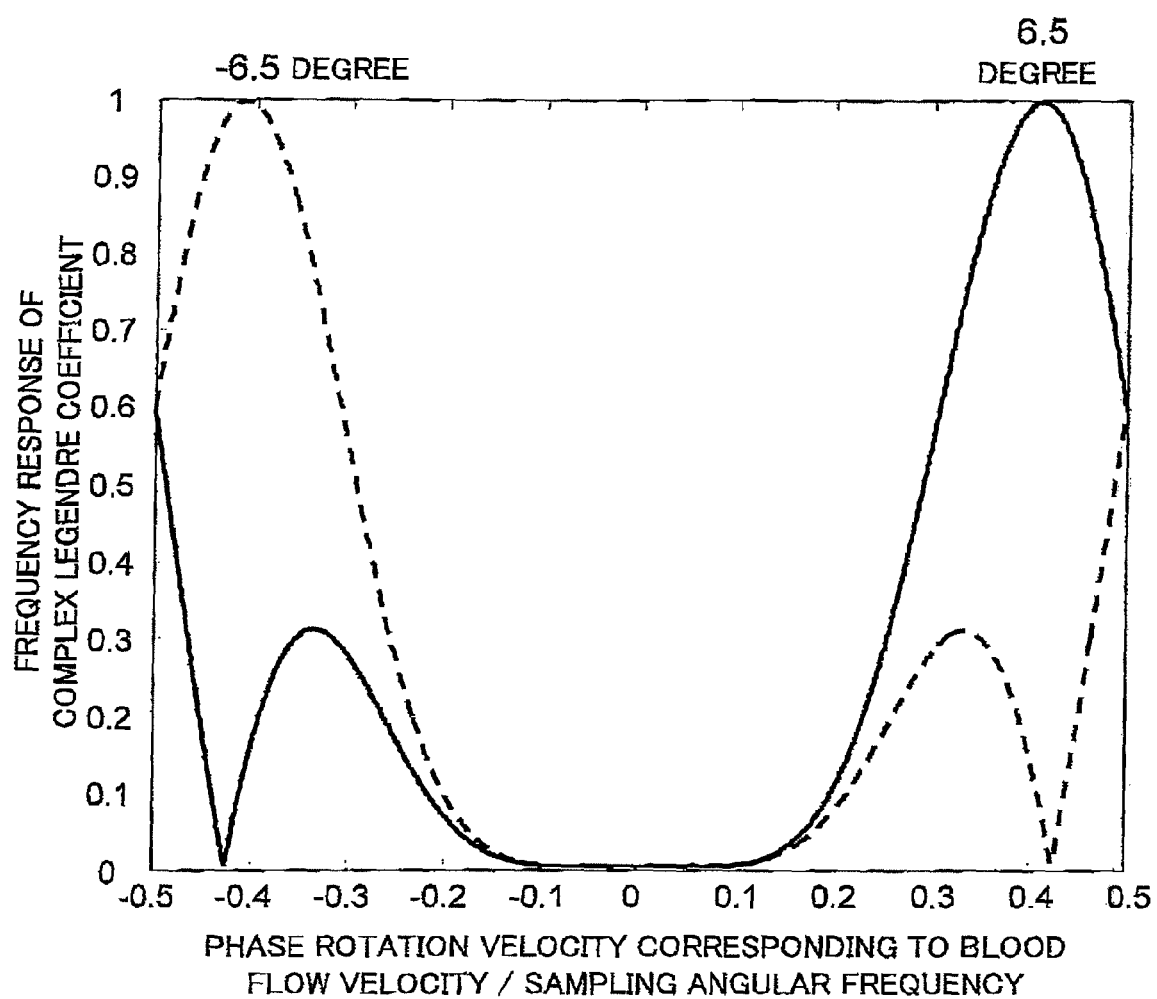
FIG. 13 shows standardized absolute values of the complex Legendre coefficients as functions of the signed frequency corresponding to the velocity.
Figure 14:
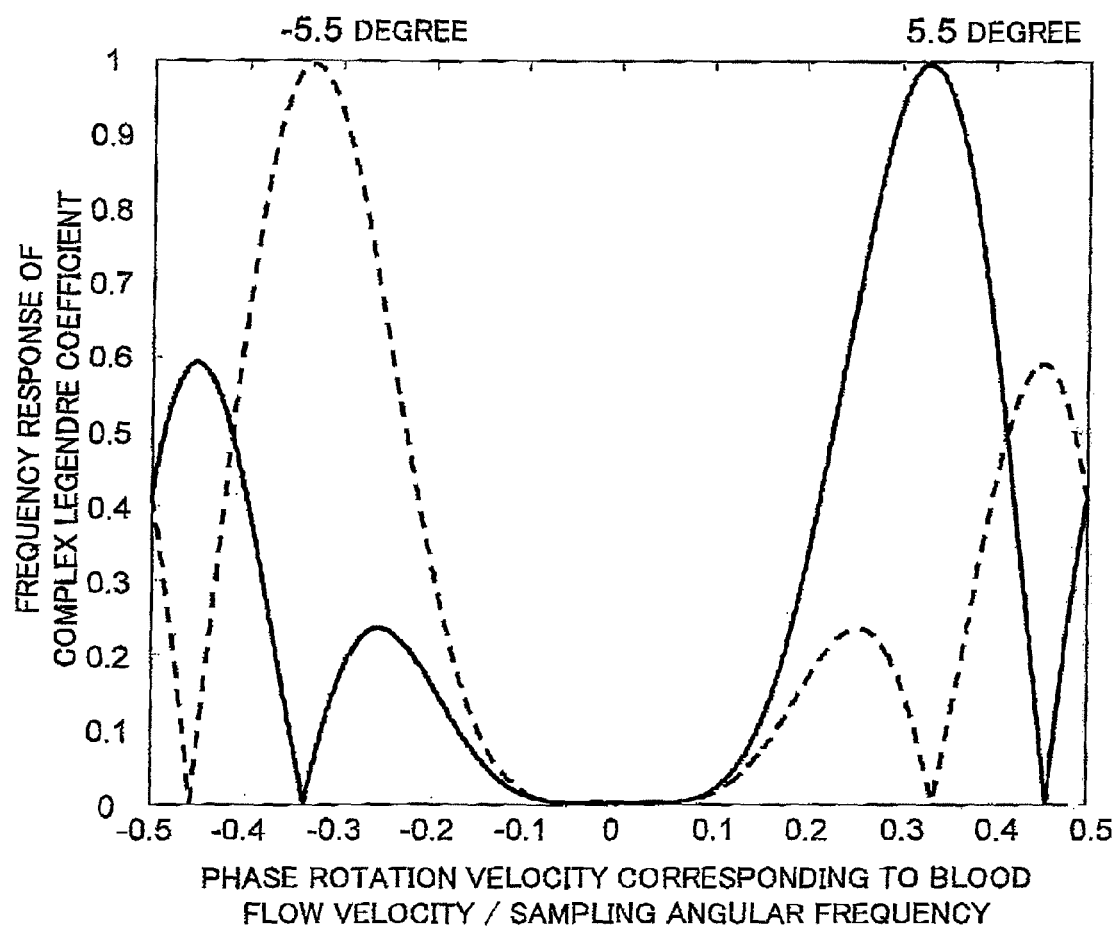
FIG. 14 shows the standardized absolute values of the complex Legendre coefficients as the functions of the signed frequency corresponding to the velocity.
Figure 15:
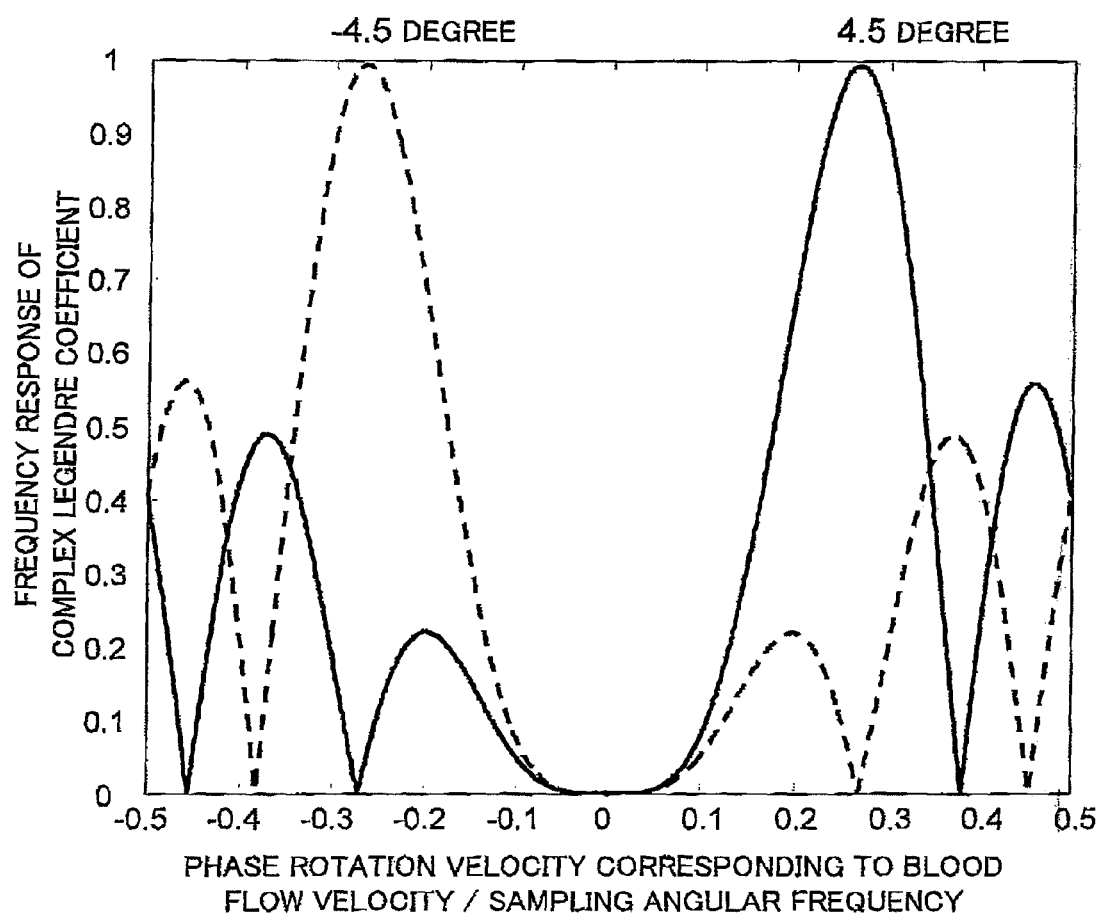
FIG. 15 shows the standardized absolute values of the complex Legendre coefficients as the functions of the signed frequency corresponding to the velocity.

In FIGS. 13 to 15, the absolute values of the complex Legendre coefficients as an output corresponding to input complex sine wave in the case of N=8 (similar to the case shown in FIGS. 10 to 12) are shown as functions of the phase rotation velocity that corresponds to the signed velocity. The figures are plotted by the absolute values of the complex Legendre coefficients standardized by the maximum values of the respective Legendre expansion coefficients. In FIG. 13, the continuous line represents C(6.5) and the broken line represents C(−6.5); in FIG. 14, the continuous line represents C(5.5) and the broken line represents C(−5.5); and in FIG. 1, the continuous line represents C(4.5) and the broken line represents C(4.5). It can be known from these figures that the complex Legendre coefficients are responding the velocity in a manner in which the sign (positive or negative) of the velocity can be distinguished. Incidentally, it has been confirmed that the complex Legendre system capable of responding the velocity in the aforesaid manner can be established in a range of N≦35.

Figure 3:
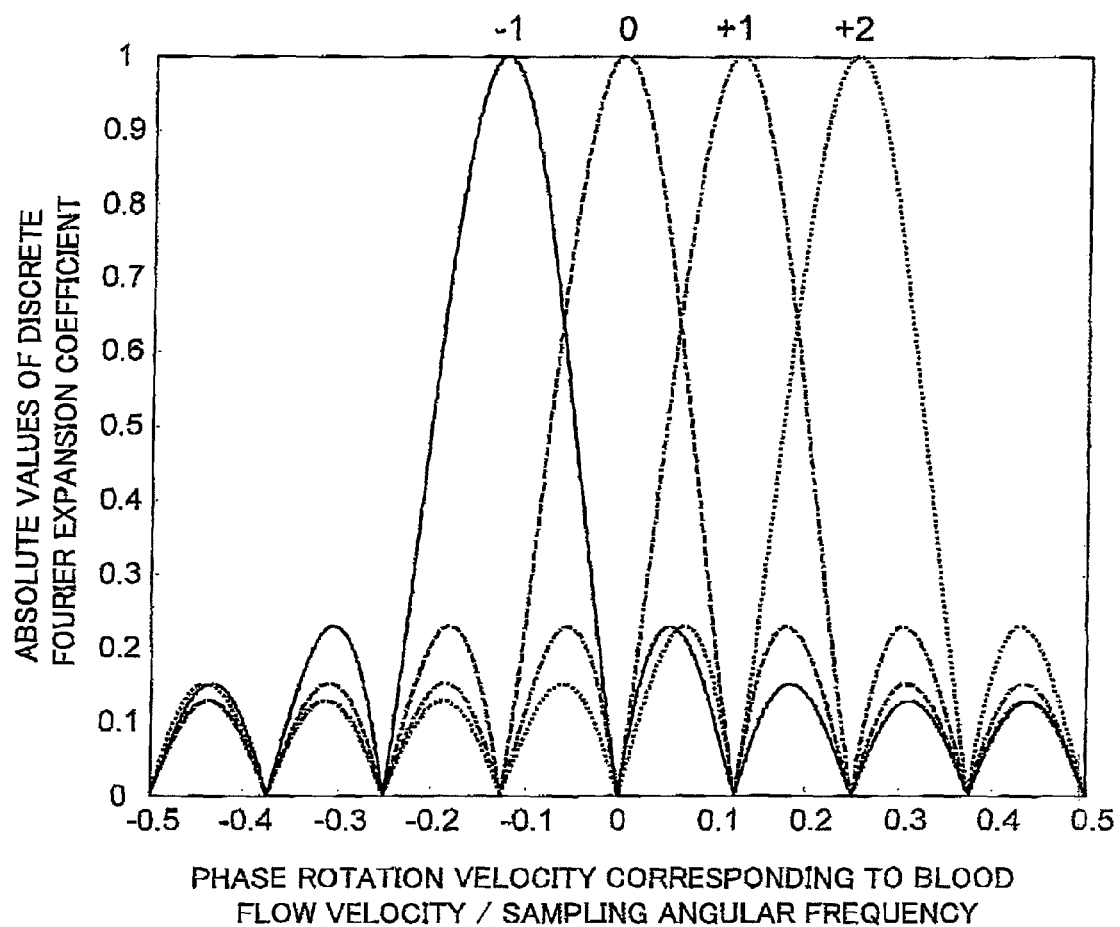
FIG. 3 shows the absolute values of the discrete Fourier expansion coefficient as functions of the signed frequency corresponding to the velocity.
Figure 4:
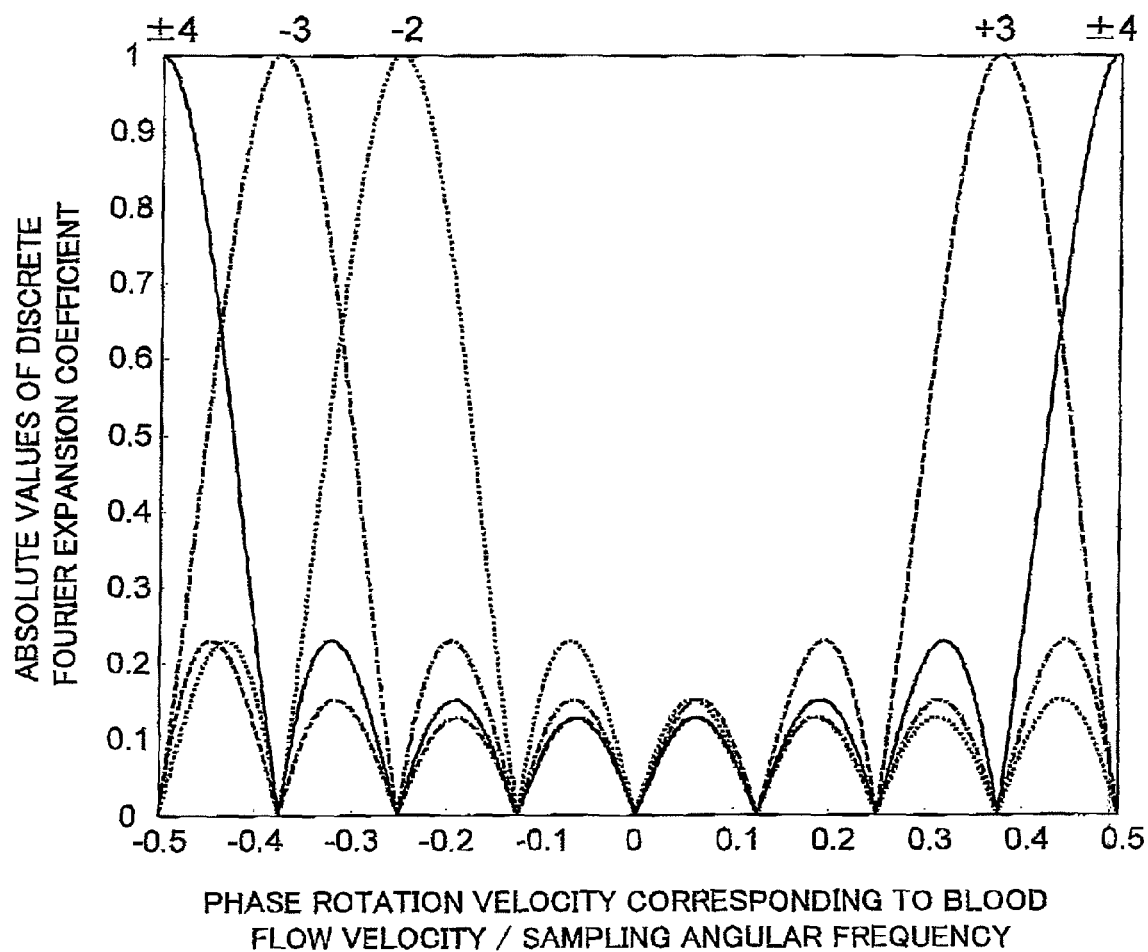
FIG. 4 shows the absolute values of the discrete Fourier expansion coefficient as functions of the signed frequency corresponding to the velocity.

The response of the complex Legendre coefficient indicated in FIGS. 13 to 15 shows extremely excellent cutoff characteristic in the vicinity of the phase rotation velocity origin (namely the Doppler frequency origin), which is the characteristic of the Legendre. expansion coefficient. But on the other hand, the response of the complex Legend re coefficient has higher frequency sidelobe level compared to the response of the Fourier expansion coefficient indicated in FIGS. 2 to 4. Specifically, the frequency sidelobe level of the Fourier expansion coefficient in examples of FIGS. 2 to 4 is about 0.2, while the frequency sidelobe level of the complex Legendre coefficient in example of FIG. 14 reaches up to approximately 0.6. High frequency sidelobe level means high probability of causing a velocity detection error when the S/N is low (namely signal level is low relative to the noise level), therefore the frequency sidelobe level is preferably to be restricted.

When generating the C(±2n) according to the A(2n), the A(2n−1) and A(2n−1) are linearly combined so that the C(±2n) reaches the maximum value at the same frequency at which the A(2n) reaches the maximum value, and the result of the linear combination is used to generate the C(±2n); and when generating the C(±(2n−1)) according to the A(2n−1), the A(2n−2) and A(2n) are linearly combined so that the C(±(2n−1)) reaches the maximum value at the same frequency at which the A(2n−1) reaches the maximum value, and the result of the linear combination is used to generate the C(±(2n−1)).

Namely, the C(±2n) and the C(±(2n−1)) can be indicated as the following equation.

$$C(\pm(2n-1))=\alpha(2n-1)\times A(2n-2)+\beta(2n-1)\times A(2n)\pm jA(2n-1)$$

where $1 \leq 2n-1 \leq N-1$; n: natural number; double signs in same order; α, β: positive real number.

$$C(\pm 2n)=A(2n)\pm j[\alpha(2n)\times A(2n-1)+\beta(2n)\times A(2n+1)] \qquad (5)$$

where $2 \leq 2n \leq N-1$; n: natural number; double signs in same order; α, β: positive real number.

Figure 16:
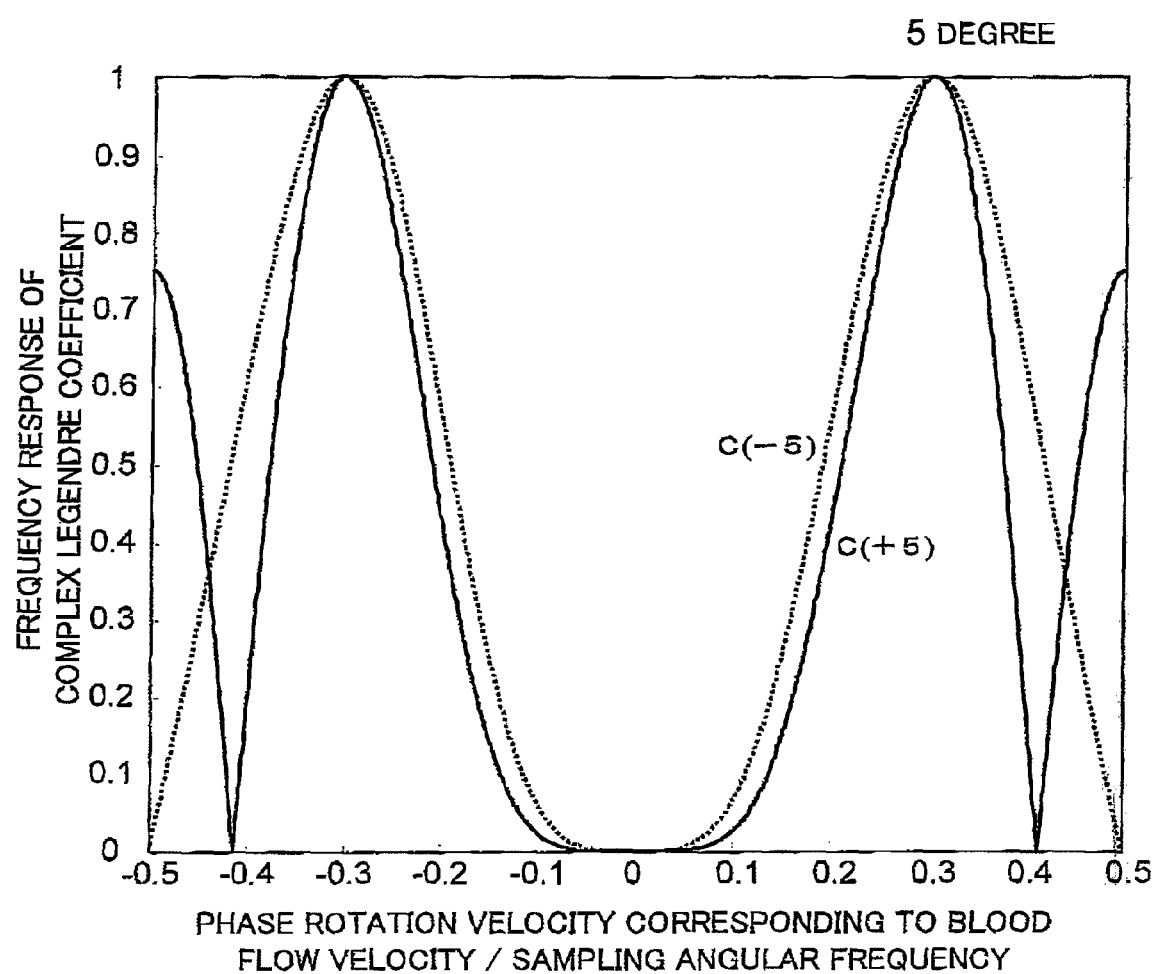
FIG. 16 shows the standardized absolute values of the Legendre expansion coefficients as the functions of the signed frequency corresponding to the velocity.
Figure 17:
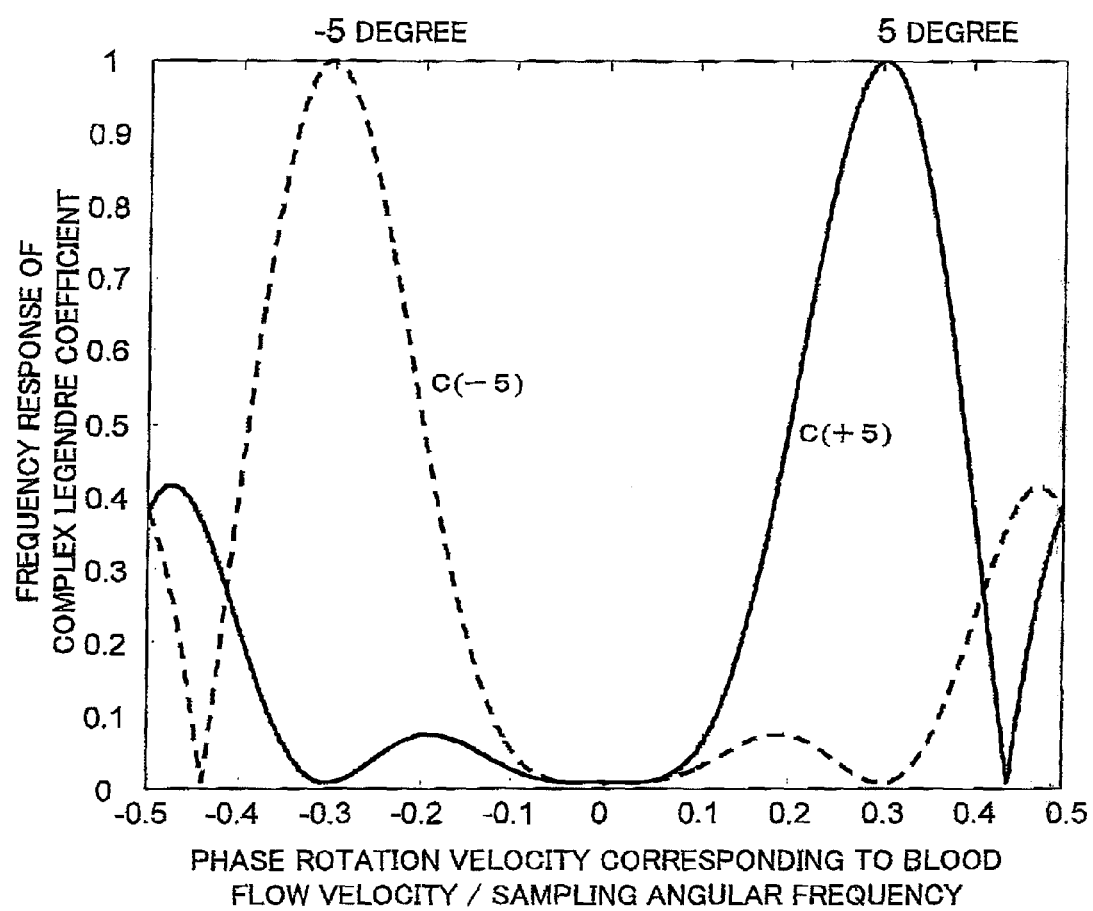
FIG. 17 shows the standardized absolute values of the complex Legendre coefficients as the functions of the signed frequency corresponding to the velocity.
Figure 18:
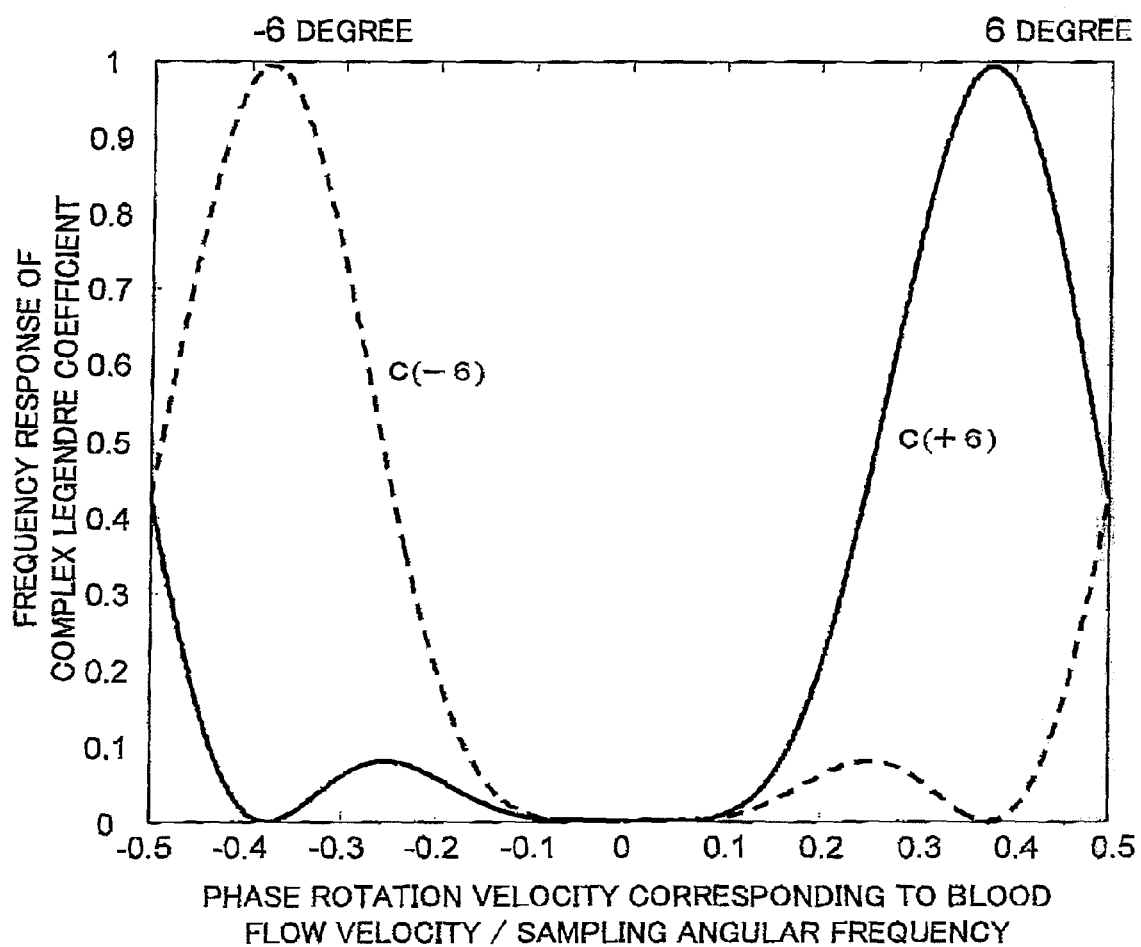
FIG. 18 shows the standardized absolute values of the complex Legendre coefficients as the functions of the signed frequency corresponding to the velocity.
Figure 19:
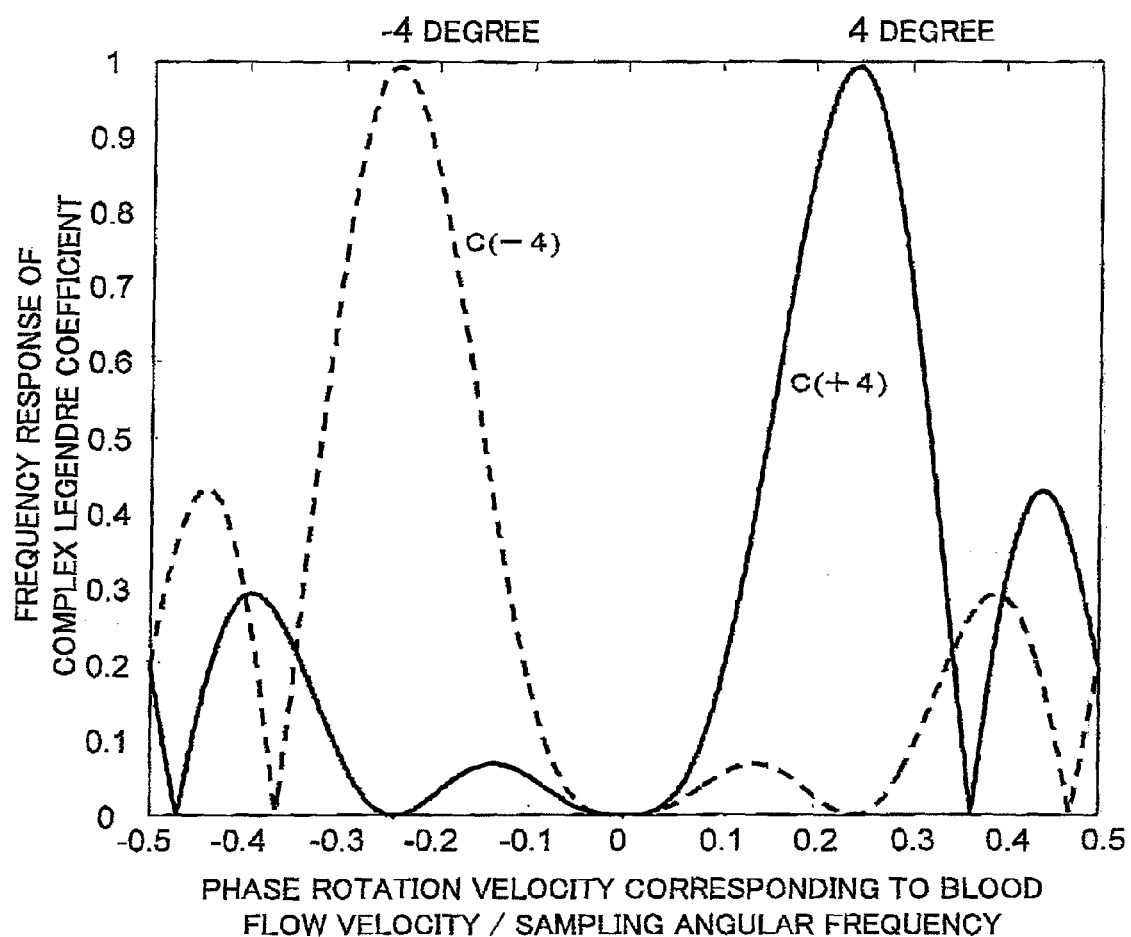
FIG. 19 shows the standardized absolute values of the complex Legendre coefficients as the functions of the signed frequency corresponding to the velocity.
Figure 20:
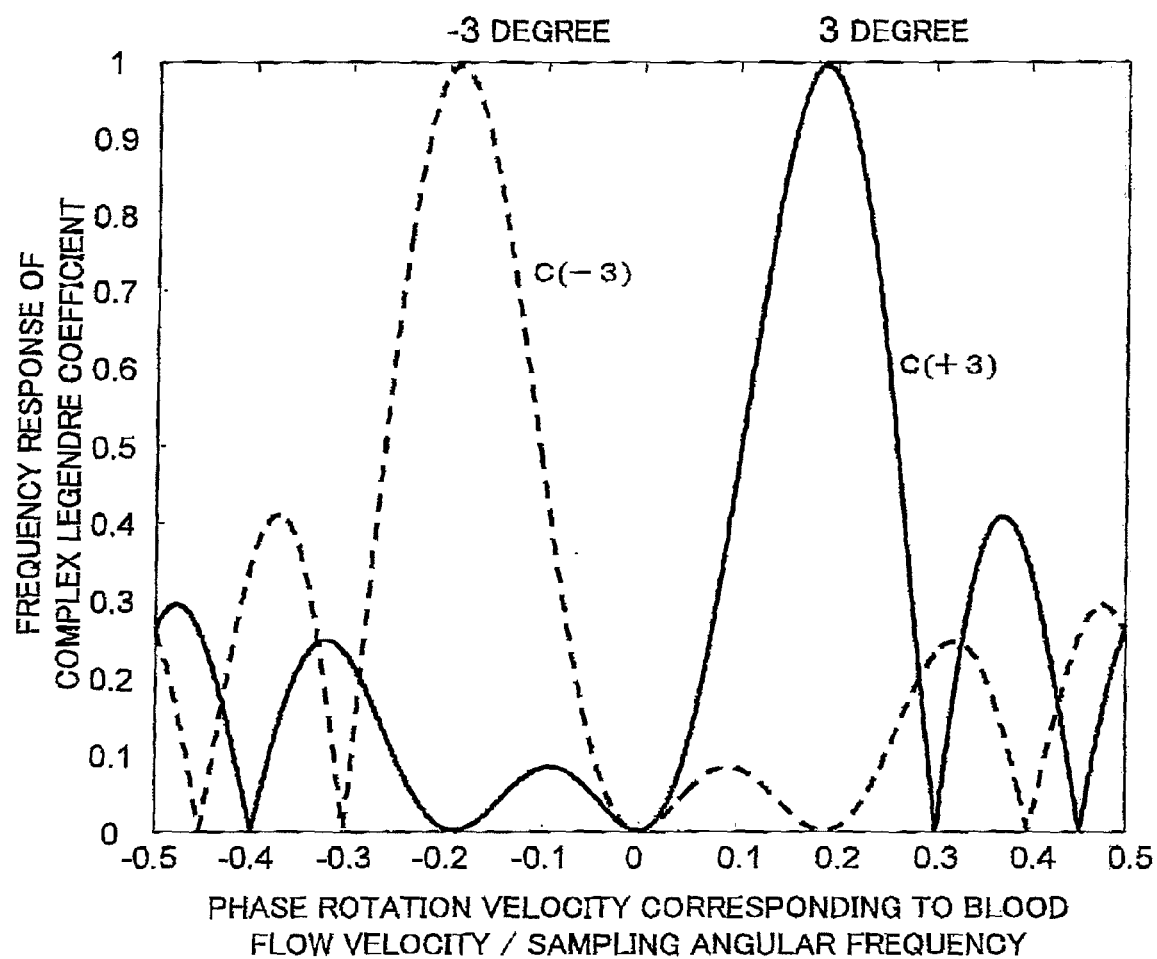
FIG. 20 shows the standardized absolute values of the complex Legendre coefficients as the functions of the signed frequency corresponding to the velocity.

FIGS. 16 and 17 show examples in which a complex Legendre coefficient C(±5) is generated according to the Legendre coefficients A(4), A(S) and A(6) in the case of N=8 (similar to the case shown in FIGS. 13 to 15). In FIG. 16, the continuous line represents a Doppler frequency response of the absolute value of the A(5). On the other hand, the dot line represents a Doppler frequency response of the absolute value of the coefficient generated by linearly combining A(4) and A(6) so that the complex Legendre coefficient C(±5) reaches the maximum value at the same frequency at which the A(5) reaches the maximum value. In FIG. 17 shows a Doppler frequency response of the absolute value of the complex Legendre coefficient C(±5), in which the real part represents a linear combination of the A(4) and A(6), and the imaginary part is the A(5). In FIG. 17, the continuous line represents C(5), and the broken line represents C(−5). The frequency sidelobe level is restricted to about 0.4. The frequency sidelobe level is considerably improved compared to that of the C(±5.5) shown in FIG. 14 and that of C(±4.5) shown in FIG. 15, in which the frequency sidelobe levels are about 0.6. FIGS. 1 to 20 respectively show Doppler frequency responses of the absolute value of the complex Legendre coefficients C(±6), C(±4) and C(±3) generated in the same manner. Similar to FIG. 17, the continuous lines represent C(6), C(4) and C(3), and the broken lines represent C(−6), C(−4) and C(−3). The frequency sidelobe levels are restricted to about 0.4. In other words, the sidelobe level is restricted from about 0.6 to about 0.4 by linearly combining the A(2n−2) and A(2n) so that the complex Legendre coefficient reaches the maximum value at the same angular frequency at which the A(2n−1) reaches the maximum value.

Figure 21:
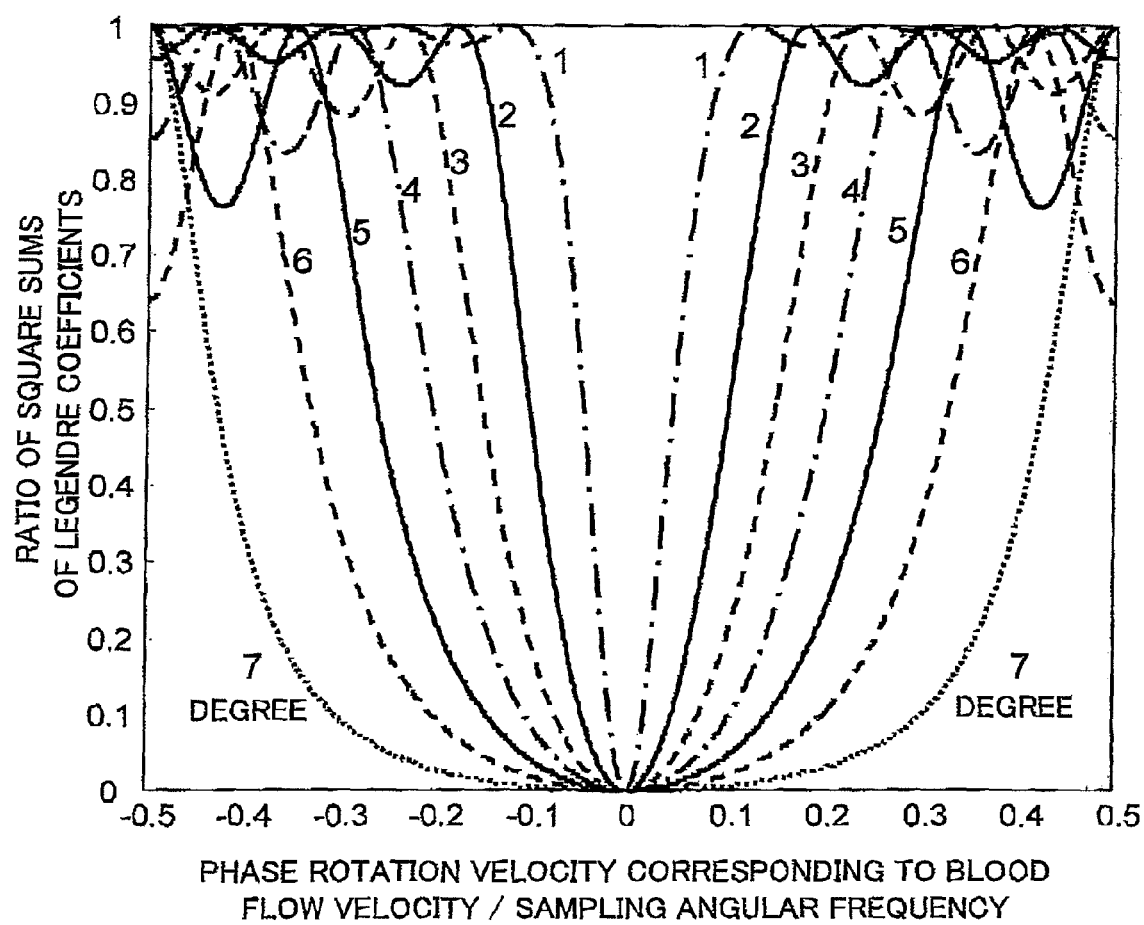
FIG. 21 shows ratios of square sum of the Legendre expansion coefficients.

When m represents a natural number, ratios R(m) of a square sum of (m−1)-th to (N−1)-th Legendre coefficients to a square sum of math to (N−1)-th Legendre coefficients are shown in FIG. 21 in the case of N=8 (similar to the aforesaid examples).

$$R(m)=[A(m)^2+\ldots+A(N-1)^2]/[A(m-1)^2+A(m)^2+\ldots+A(N-1)^2] \qquad (6)$$

where $1 \leq m \leq N-1$.

Figure 22:
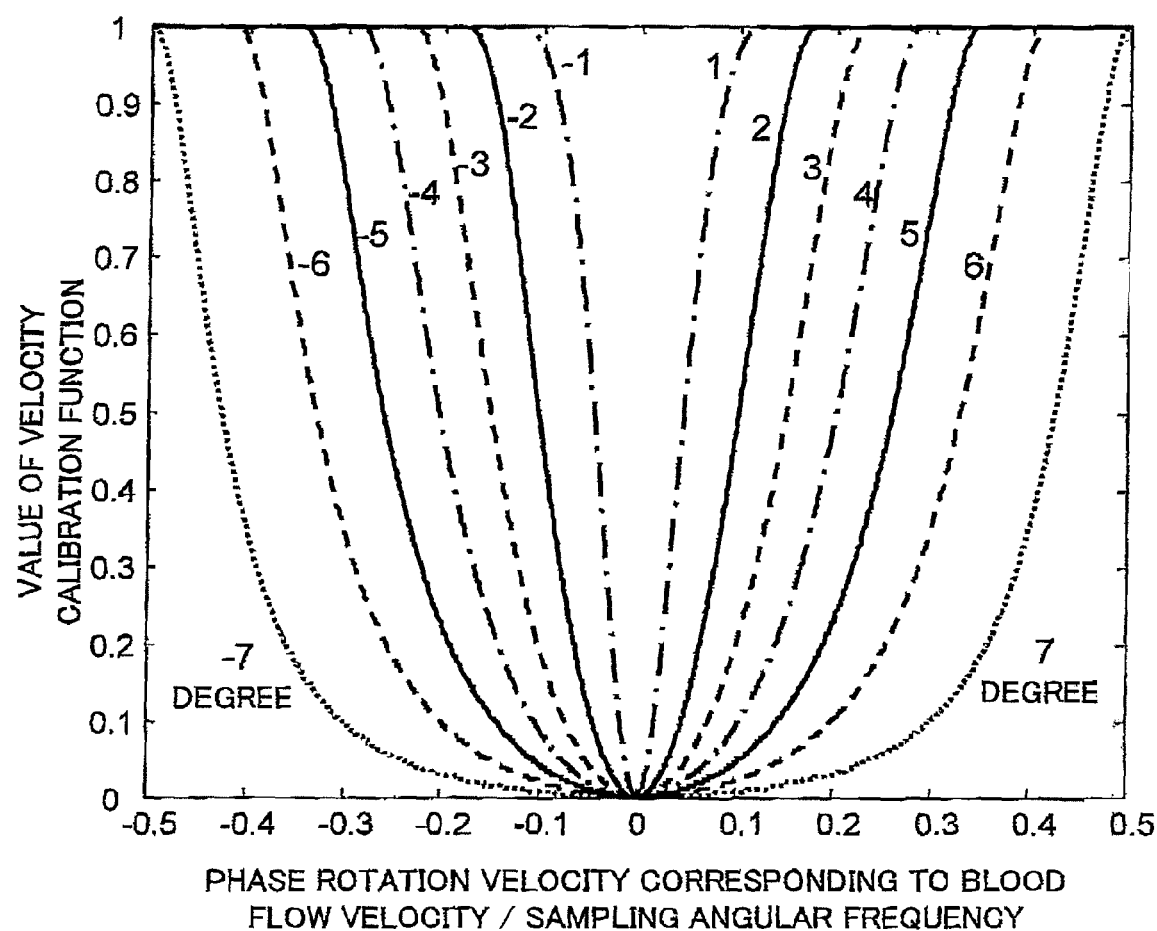
FIG. 22 shows velocity calibration curves obtained from the ratios of the square sum of the Legendre expansion coefficients.

These curves increase monotonously with the augmentation of the distance from the Doppler frequency origin until reaching the maximum value, then ripple. FIG. 22 shows velocity calibration curves obtained by taking the monotonically increasing parts, If the degree of the complex Legendre coefficient having the maximum absolute value is obtained, then the Doppler velocity can be calculated from the ratio of the square sum of the Legendre coefficients by using the velocity calibration curve corresponding to the obtained degree.

When the clutter signal (which has amplitude incomparably greater than that of the moving reflection object echo to be detected and analyzed) drifts, the velocity detection/analysis can be performed by using a complex Legendre coefficient system in which the coefficients having lower degrees are sequentially removed in order of C(±1), C(±2) . . . , as the magnitude of the drift increases. By controlling the cutoff degree of the Legendre coefficient in such a manner, the velocity detection/analysis of the moving reflection object can be performed while the effect of the clutter signal can be restricted.

First Embodiment

A first embodiment of the present invention will be described as below.

Figure 23:
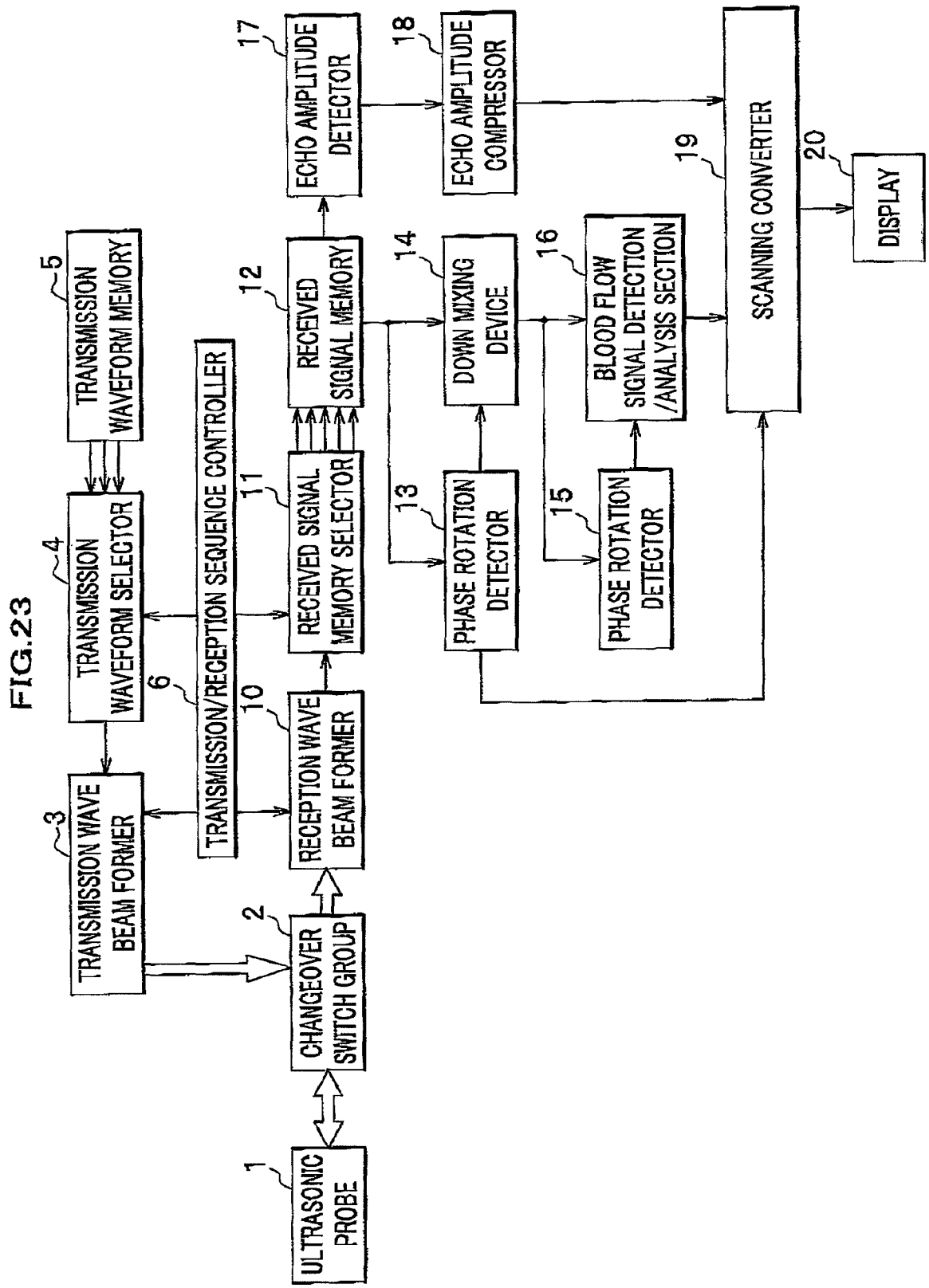
FIG. 23 is block diagram showing a configuration of an ultrasonic diagnostic apparatus using a velocity measuring device according to a first embodiment.

FIG. 23 is a block diagram showing an ultrasonic diagnostic apparatus using a velocity measuring device, which is the first embodiment of the present invention, the ultrasonic diagnostic apparatus having a blood flow drawing function. Each of elements which constitute an ultrasonic probe is respectively connected to a transmission wave beam former 3 and a reception wave beam former 10 through a changeover switch group 2. The transmission wave beam former 3 generates a signal using a waveform selected and read out by a transmission waveform selector 4 from a transmission waveform memory 5 under control of a transmission/reception sequence controller 6, the signal becoming an ultrasonic pulse having directivity when being transmitted through each of the elements. The signal is converted into the ultrasonic pulse by each of the elements and transmitted to a living body. After being reflected or scattered in the living body, the ultrasonic echo signal returned to the ultrasonic probe 1 is received by each of the elements and converted into an electronic signal. The reception wave beam former 10 applies a delay time to the received wave signals and adds the received wave signals to each other. Under the control of the transmission/reception sequence controller 6, the time series signals obtained by performing the delay addition are once written into a bank of a received signal memory 12, selected by a received signal memory selector 11, read out from the bank after N time series signals to receive Doppler signal analysis have been read in, and processed in phase rotation detectors 13, 15, a down mixing device 14, and a blood flow signal detection/analysis section 16 so as to detect and analyze the velocity.

Of the N time series received signals being read out, the parts having the same time phase with respective pulse transmission times as reference are arranged in order of the transmission time and processed. A velocity detection algorithm will be discussed below with reference to FIG. 23 and the flowchart of FIG. 24. First, the phase rotation detector 13 obtains the phase rotation from the time series signals which include clutter signal. The most typical method for detecting the phase rotation is calculating the P(n) indicated as the following equation (7) based on the adjacent time series complex signals S(n), S(n+1) arranged in order of n=1, . . . , N, and obtaining the average phase rotation velocity from the phase of the value Pa of the average P(n).

$$P(n)=S(n+1)S(n)^*/\|S(n+1)\|\|S(n)\| \quad (7)$$

where n-1, . . . N.

Herein, the S(n)* the complex conjugate of the S(n), and the ||S(n)|| is the absolute value of the S(n). Since the amplitude of the clutter echo signal is generally incomparably greater than that of the blood flow echo signal, the Pa is substantially the average value of the phase rotation of the clutter echo signal. In other words, the clutter average velocity is calculated based on the average value of the phase difference between adjacent samples (S1 of FIG. 24). Further, the time series complex signal S(n) can be obtained by multiplying the received echo signal by two carrier frequency signals different by 90° in phase.

The down mixing device 14 performs mixing process by using the obtained average value Pa or by using a space average value in the peripheral region of the Pa so that the average value of the phase rotation of the echo signal becomes zero. In other words, the phase rotation caused by the clutter average velocity is cancelled by the down mixing (S2 of FIG. 24). Namely, the Sd(n) indicated as the following equation can be obtained from the S(n) and Pa.

$$Sd(n)=S(n)Pa^{*n}(n-1, \ldots, N) \quad (8)$$

By performing the down mixing processing, the process in a latter stage for restricting the clutter signal can be effectively performed.

Based on the time series complex signals Sd(n) and Sd(n+1), which are the obtained adjacent samples, the phase rotation detector 15, similar to the phase rotation detector 13, calculates the Pd(n) indicated as the following equation.

$$Pd(n)=Sd(n+1)Sd(n)^*/\|Sd(n+1)\|\|Sd(n)\| \quad (9)$$

where n=1, . . . , N−1.

Figure 24:
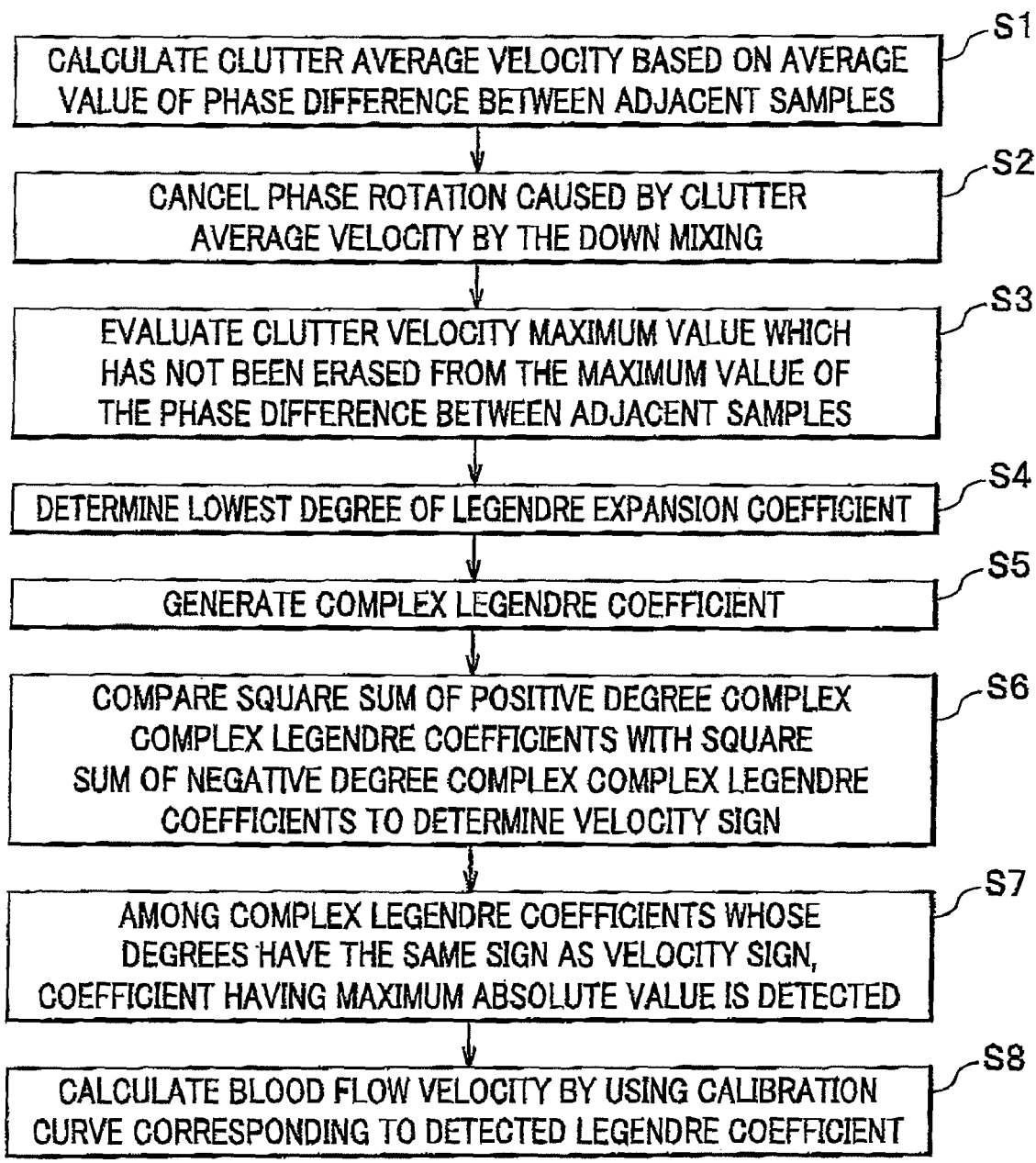
FIG. 24 is a flowchart showing an example of a velocity detection algorithm of the present embodiment.

The clutter velocity maximum value which has not been erased from the maximum value of the phase difference between adjacent samples is evaluated (S3 of FIG. 24). In order to control the cutoff characteristic of the blood flow signal detection/analysis section 16 in accordance with the maximum value of the phase difference, the lowest degree of the Legendre expansion coefficient is determined (S4 of FIG. 24). In other words, when the maximum value of the phase difference is larger, the cutoff degree M of the Legendre expansion coefficient is set higher, so that the clutter components can be effectively restricted.

Here, the operation of the blood flow signal detection/analysis section 16, which shows the character of the present embodiment, will be described in more detail below. The input time series signals Sd(1), . . . Sd(N) are firstly expanded into 0-th to (N−1)-th discrete Legendre function as shown in FIGS. 8 and 9, and the expansion coefficients A(0), . . . , A(N−1) are obtained. The calculation can be facilitated by the following matrix. If a n-th Legendre function is expressed by a row vector L(n) and an N×N matrix LL is generated by arranging the row vector in order of n=0, . . . , (N−1), then a matrix for obtaining a column vector A whose elements are A(0), . . . , A(N−1) from a column vector Sd whose elements are Sd(1) . . . , Sd(N) can be obtained as the following equation.

$$F=(L\cdot{}^tLL)^{-1}LL \quad (10)$$

Here, the ${}^tLL$ is the transposed matrix of the LL, and the $LL^{-1}$ is the inverse matrix of the LL. If the matrix is prepared previously, the Legendre expansion coefficient can be quickly obtained by calculating the following matrix.

$$A=F\cdot Sd \quad (11)$$

From the expansion coefficients A(0), . . . , A(N−1), the complex Legendre coefficient of C(±1) . . . , C(±(N−1)) can be generated according to the equation (5) (S5 of FIG. 24). In other words, the Legendre expansion coefficient can be obtained by multiplying a vector FF by the column vector Sd(n) whose elements are the time series signals, the vector FF being calculated by the following steps: a step of expressing the a n-th Legendre function as the row vector L(n), generating the N×N matrix LL by arranging the row vector in order of n=0, . . . , (N−1) in column-wise and transposing the N×N matrix LL to obtain a transposed matrix tLL; a step of performing a multiplication where the N×N matrix LL is a multiplicand and the transposed matrix tLL is a multiplier and calculating an inverse matrix $(LL\cdot tLL)^{-1}$ of the product of the multiplication; and a step of performing a multiplication where the inverse matrix $(LL\cdot tLL)^{-1}$ is a multiplicand and the N×N matrix LL is a multiplier. In addition to the above, the lowest degree (the cutoff degree M) of the Legendre expansion coefficient is determined according to the maximum value of the phase difference (S4 of FIG. 24), and the lower degree complex Legendre coefficients from C(±1) to C(±(M+1)) are dismissed.

Next, the non-dismissed square sum of the positive degree complex Legendre coefficients is compared to the non-dismissed square sum of the negative degree complex Legendre coefficients to determine the velocity sign (S6 of FIG. 24). Specifically, the sign of the degree having larger comparison result is determined to be the velocity sign. Further, among the complex Legendre coefficients whose degrees have the same sign as the velocity sign, the coefficient having maximum absolute value is detected (S7 of FIG. 24). Specifically, among the positive degree complex Legendre coefficients (if the degree is positive), the negative degree complex Legendre coefficients (if the degree is negative) and the Legendre coefficient whose maximum degree is (N−1), the coefficient having maximum absolute value is detected.

Further, the blood flow velocity is calculated using the calibration curve corresponding to the detected Legendre coefficient (S8 of FIG. 24). Namely, the Doppler velocity is obtained according to the ratio of the square sum of (m−1)-th to (N−1)-th Legendre coefficients to the square sum of m-th to (N−1)-th Legendre coefficients, by using the velocity calibration curve corresponding to the degree (see FIG. 22).

The blood flow velocity signal is input into a scanning converter 19 together with the echo signal of the stationary organ obtained by an echo amplitude detector 17 and an echo amplitude compressor 18. The scanning converter generates and controls the input signals so that the input signals are properly overlapped and displayed two-dimensionally or three-dimensionally on a display 20.

The operation of the Doppler velocity measuring device of the present embodiment will be described below, in comparison with the conventional method. The comparison is based on a case where the amplitude of the clutter echo signal is 300 times of that of the blood flow echo, and clutter has an initial velocity of zero and is brought into clutter velocity at a predetermined acceleration. A numerical value calculation simulation was performed in the case where the number of the time series signals is 8 (namely, N=8), and the results are compared with other. A method that uses a low frequency cutoff filter as shown in FIG. 6 as the MTI filter was chosen as an example of the conventional method. In the latter stage of the low frequency cutoff filter, the velocity calculation process is performed by the blood flow signal detection/analysis section 16 using the same method as used for obtaining the phase rotation average value Pa by the equation (5). Further, the comparison was also done in the case where the MTI filter was compared to the case shown in FIG. 5 where MTI filter is replaced with the polynomial regression filter as shown in FIG. 5. Similar to the method of the present invention, the cutoff degree M was controlled according to the output signal of the phase rotation detector 15.

Figure 25:
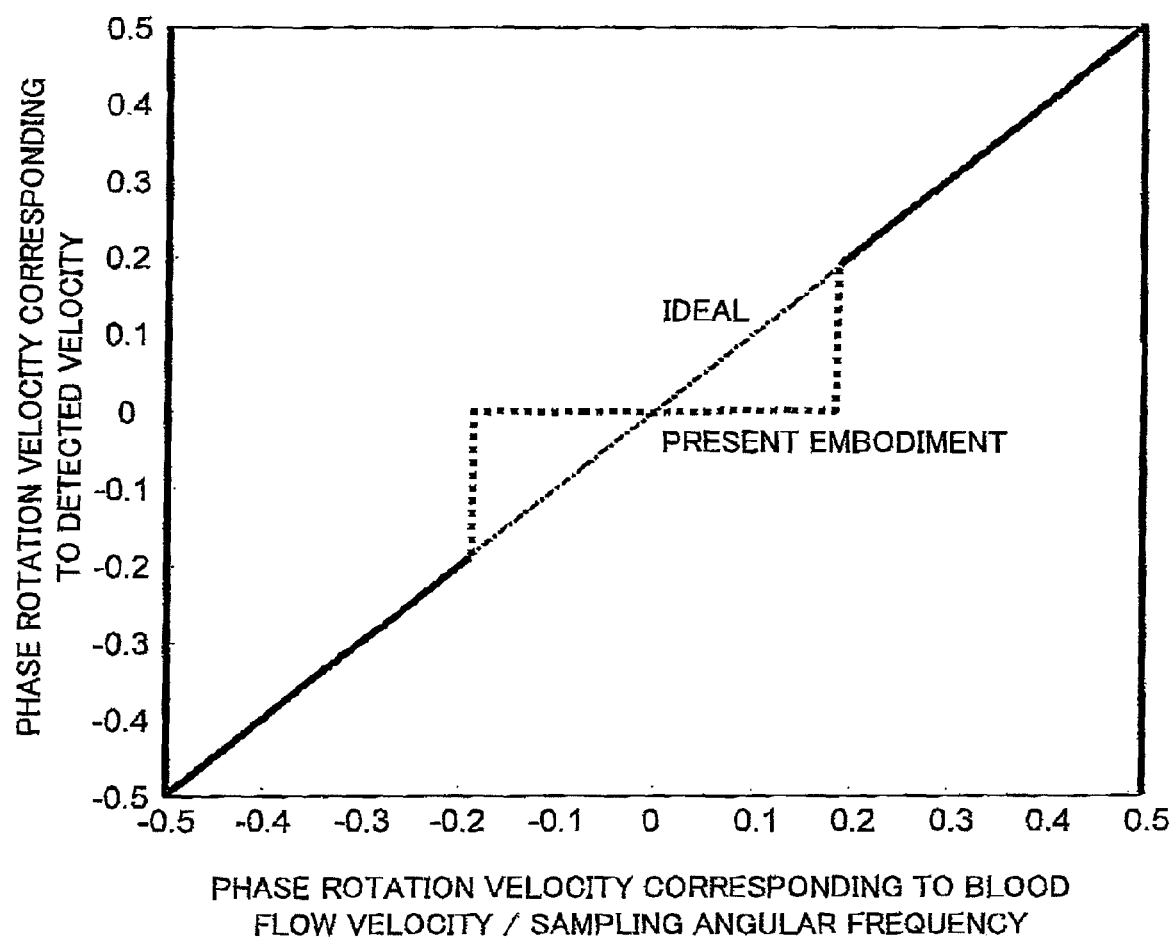
FIG. 25 shows an example of a velocity detection result using the method of the present embodiment.
Figure 26:
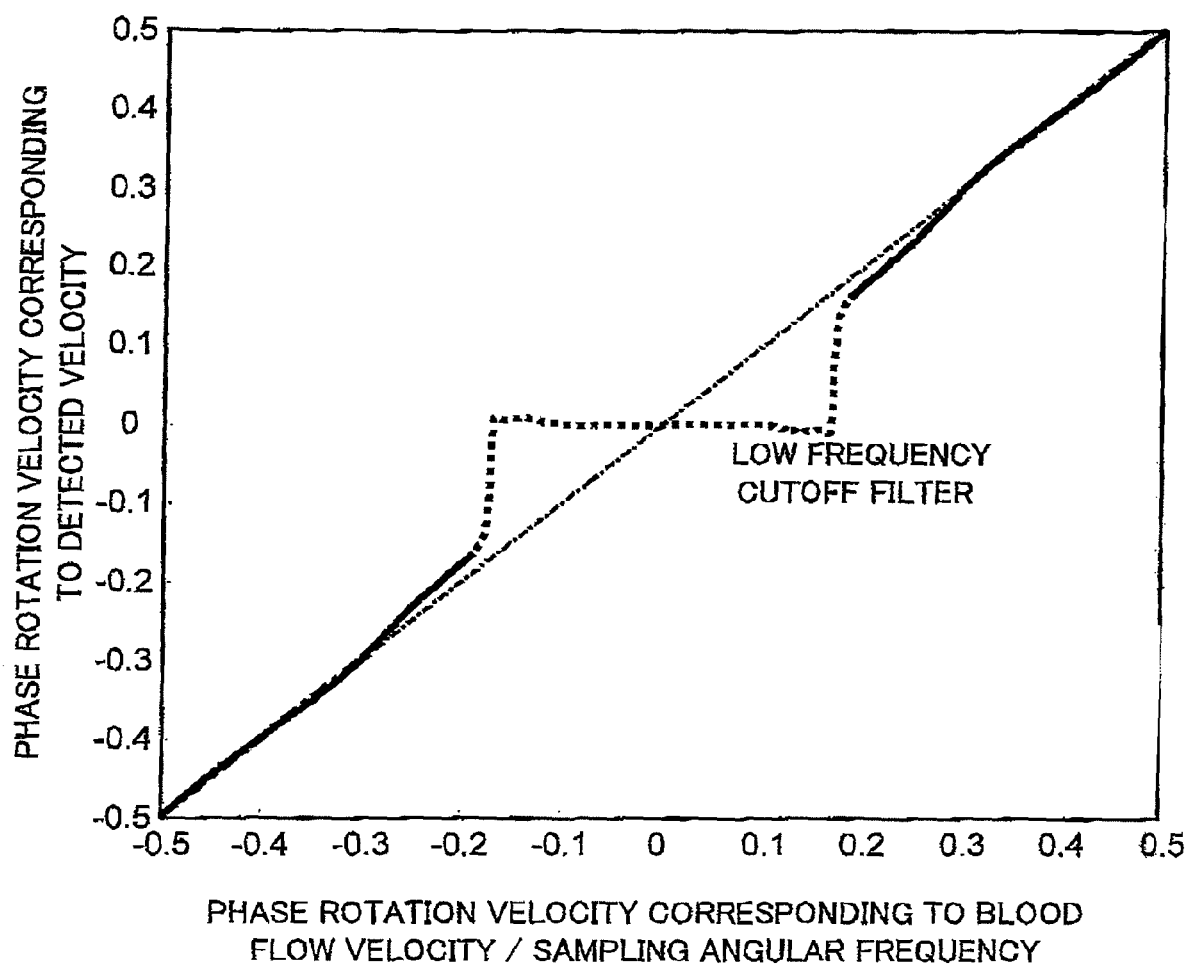
FIG. 26 shows an example of the velocity detection result using a conventional method.
Figure 27:
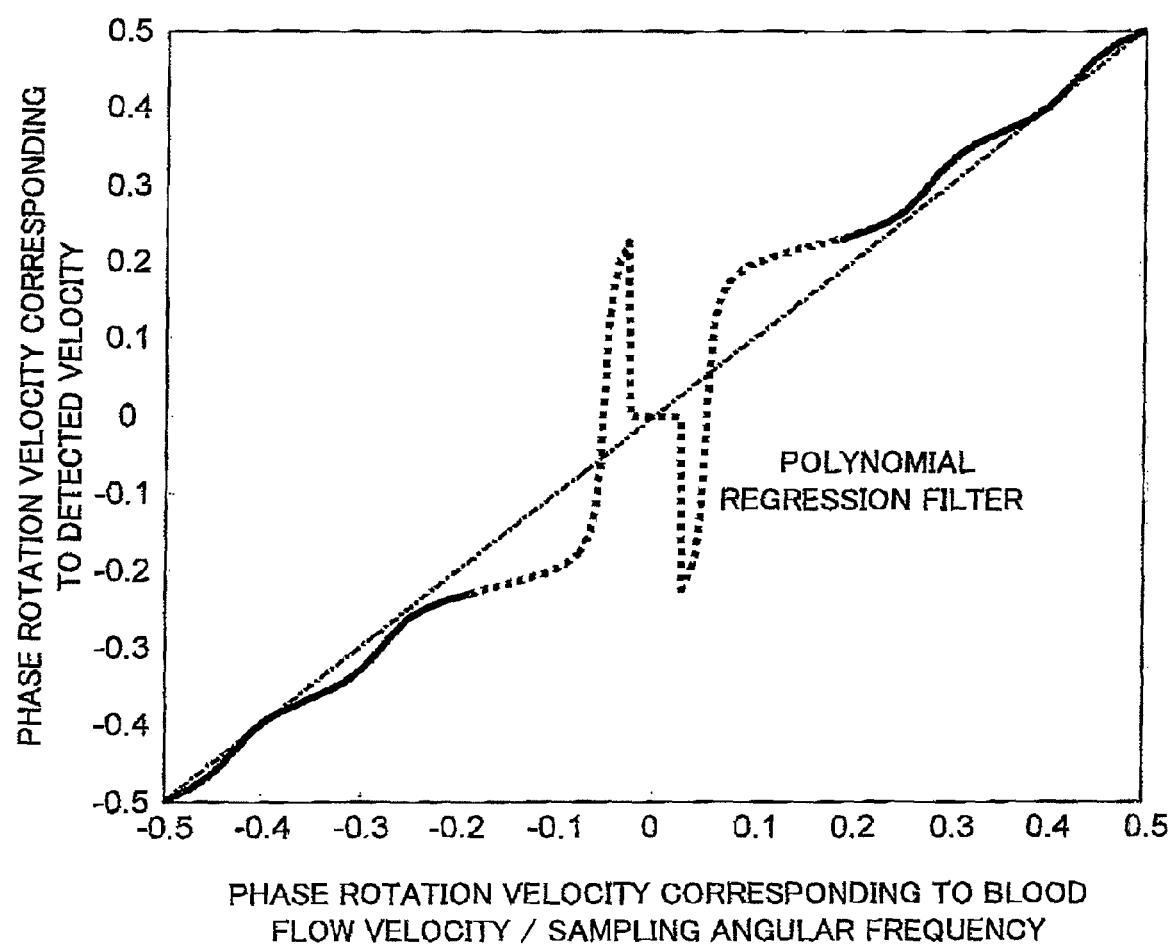
FIG. 27 shows an example of the velocity detection result obtained by using the polynomial regression filter.

FIGS. 25 to 27 respectively show the velocity detection results obtained by using the method of the present embodiment, by using the method of the low frequency cutoff filter and by using the method of the polynomial regression filter, in the case where the final attainable velocity of the clutter is 0.8% of the Nyquist limit velocity. The horizontal axis represents the blood flow velocity that is an input value, and the longitudinal axis represents the detected velocity that is an output value. The part within an effective velocity detecting range is indicated by a continuous line, and the part beyond the effective velocity detecting range is indicated by a dot line. Further, the dot and dash line indicates an ideal case. In the case where the clutter velocity is low, all the aforesaid methods can obtain substantially precise velocity analysis result, however the error caused by the method of the present embodiment is the smallest.

Figure 28:
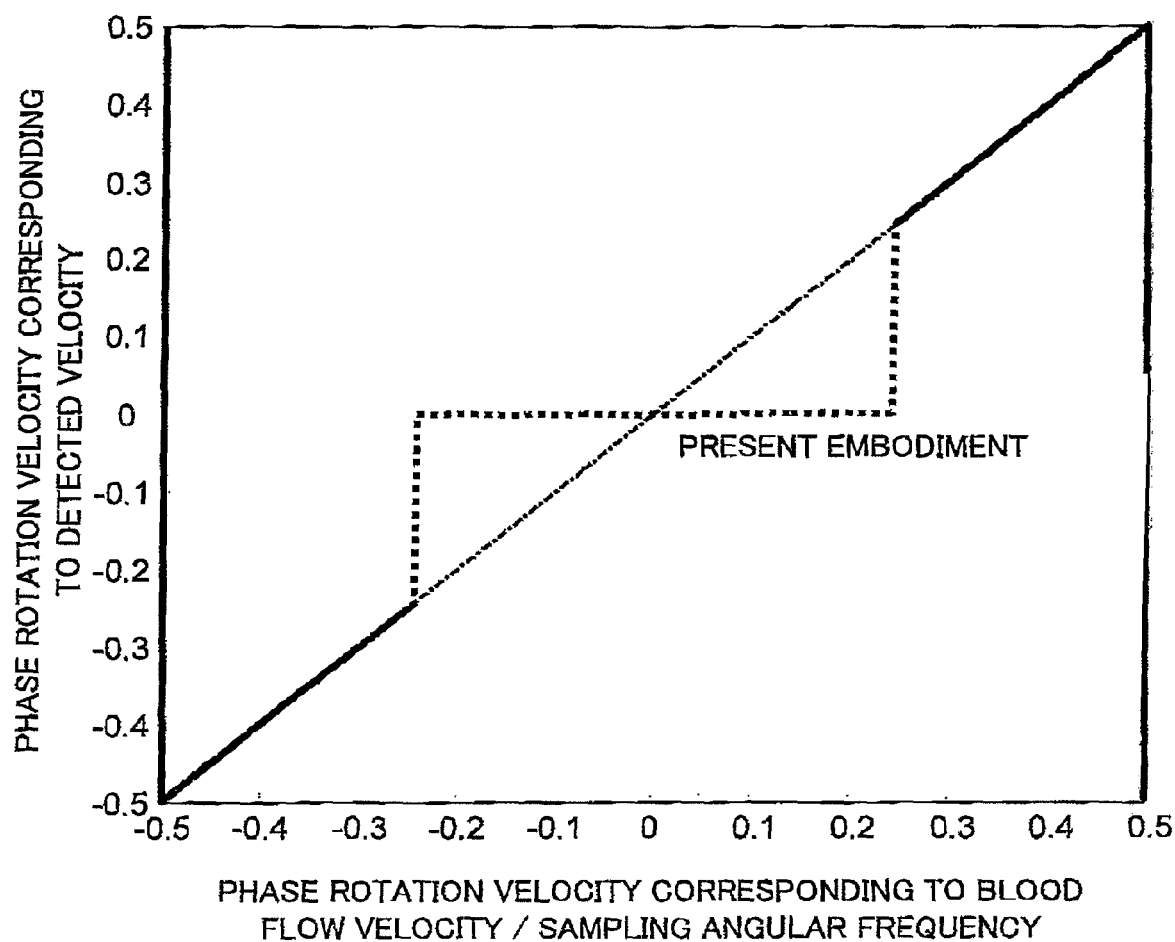
FIG. 28 shows an example of the velocity detection result obtained by using the method of the present embodiment.
Figure 29:
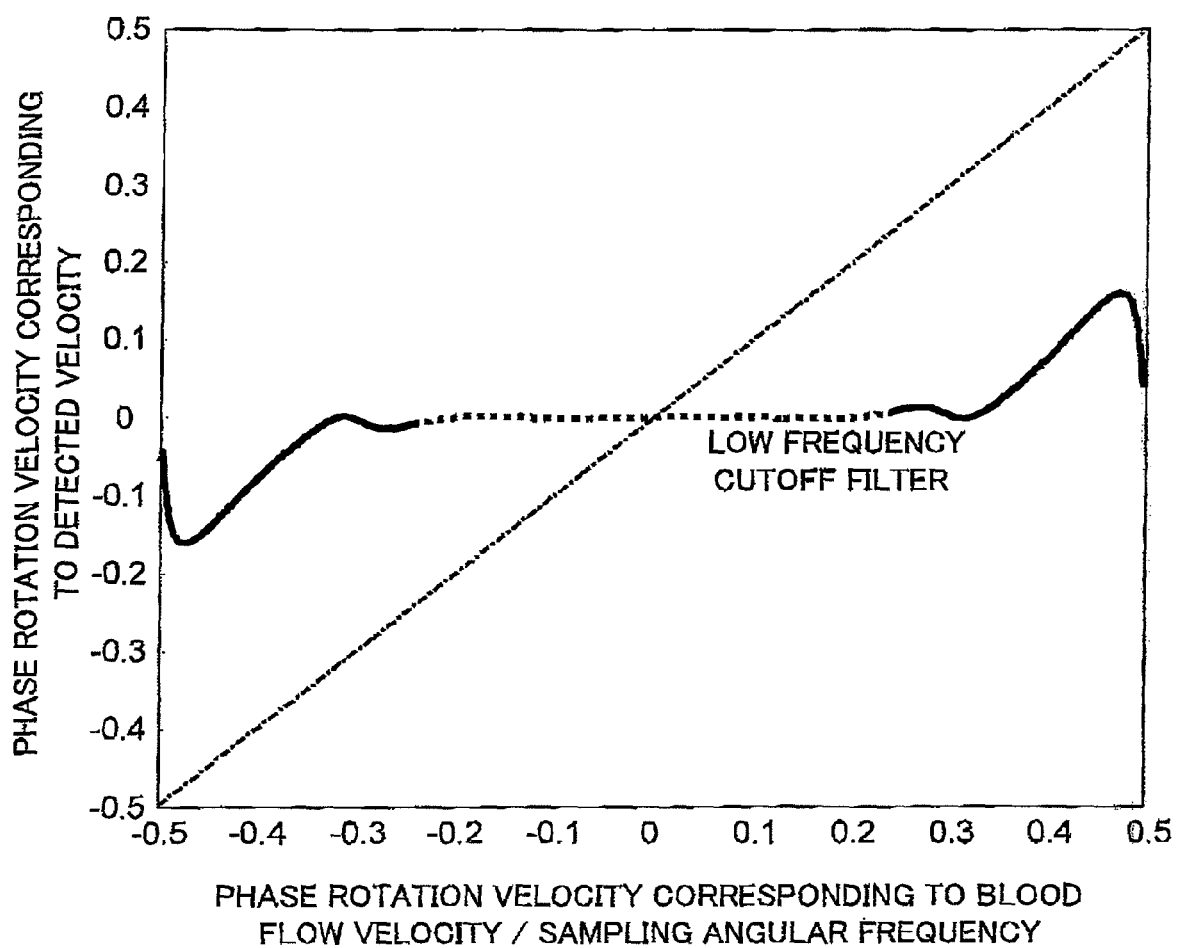
FIG. 29 shows an example of the velocity detection result obtained by using the conventional method.
Figure 30:
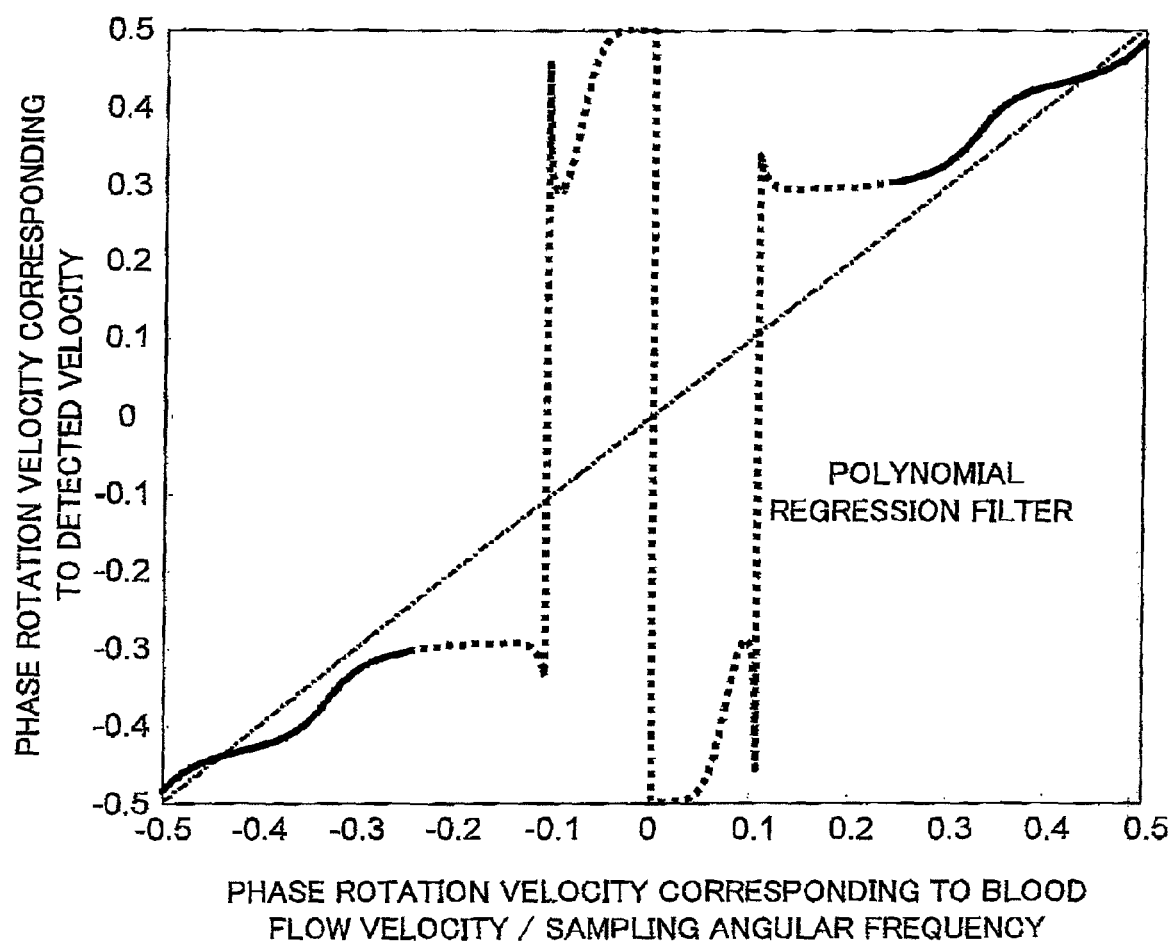
FIG. 30 shows an example of the velocity detection result obtained by using the polynomial regression filter.

Similarly, FIGS. 28 to 30 respectively show the velocity detection results obtained by using the method of the present embodiment, by using the method of the low frequency cutoff filter and by using the method of the polynomial regression filter, in the case where the final attainable velocity of the clutter reaches to 3% of the Nyquist limit velocity. In such a clutter velocity zone, the velocity detection using the low frequency cutoff filter almost can not be performed. The method using the polynomial regression filter does not cause large error within the effective velocity detecting range, but causes large error when the blood flow velocity becomes lower than the effective velocity detecting range, and therefore this method can not be used unless some kind of countermeasures are taken. In contrast, the method of the present embodiment not only provides a precise velocity detection result within the effective velocity detecting range, but also unreservedly outputs a detected velocity of zero when the blood flow velocity becomes lower than the effective velocity detecting range. Thus, the character of the velocity measuring device of the present embodiment is that it outputs the precise velocity detection result within the effective velocity detecting range, and outputs a detected velocity of zero when the blood flow velocity becomes lower than the effective velocity detecting range. Using such a character, whether or not the present embodiment is performed can be known without checking the inner constriction of the selected velocity measuring device.

Figure 31:
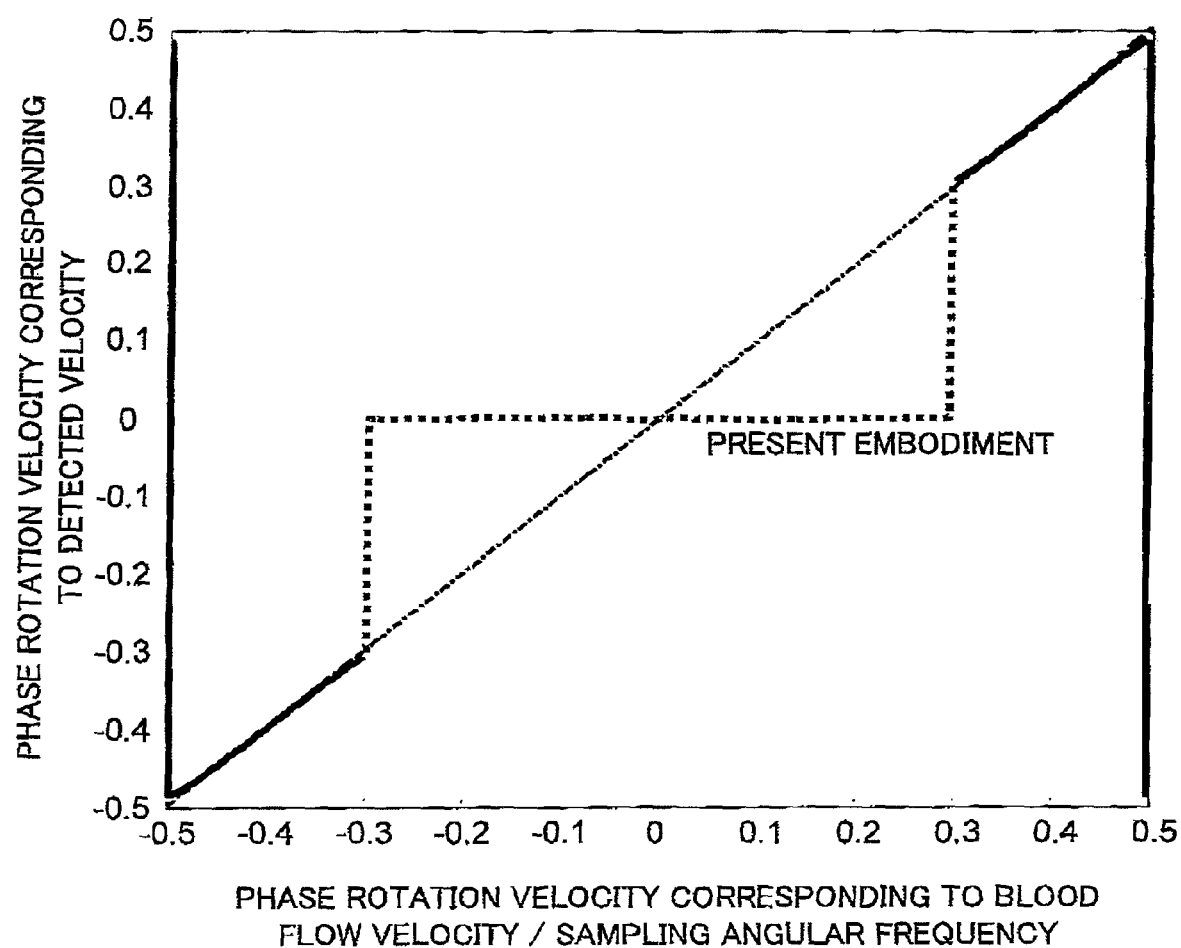
FIG. 31 shows an example of the velocity detection result obtained by using the method of the present embodiment.
Figure 32:
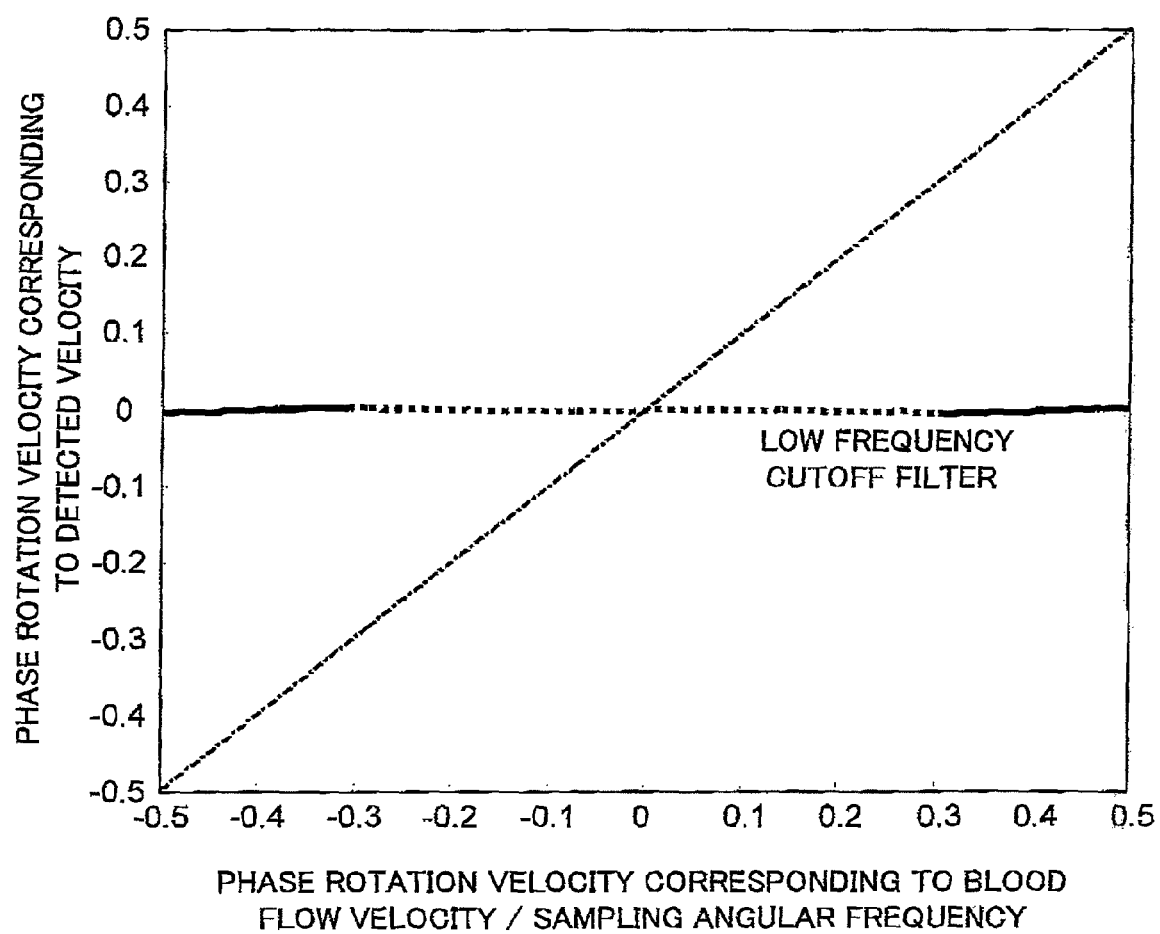
FIG. 32 shows an example of the velocity detection result obtained by using the conventional method.
Figure 33:
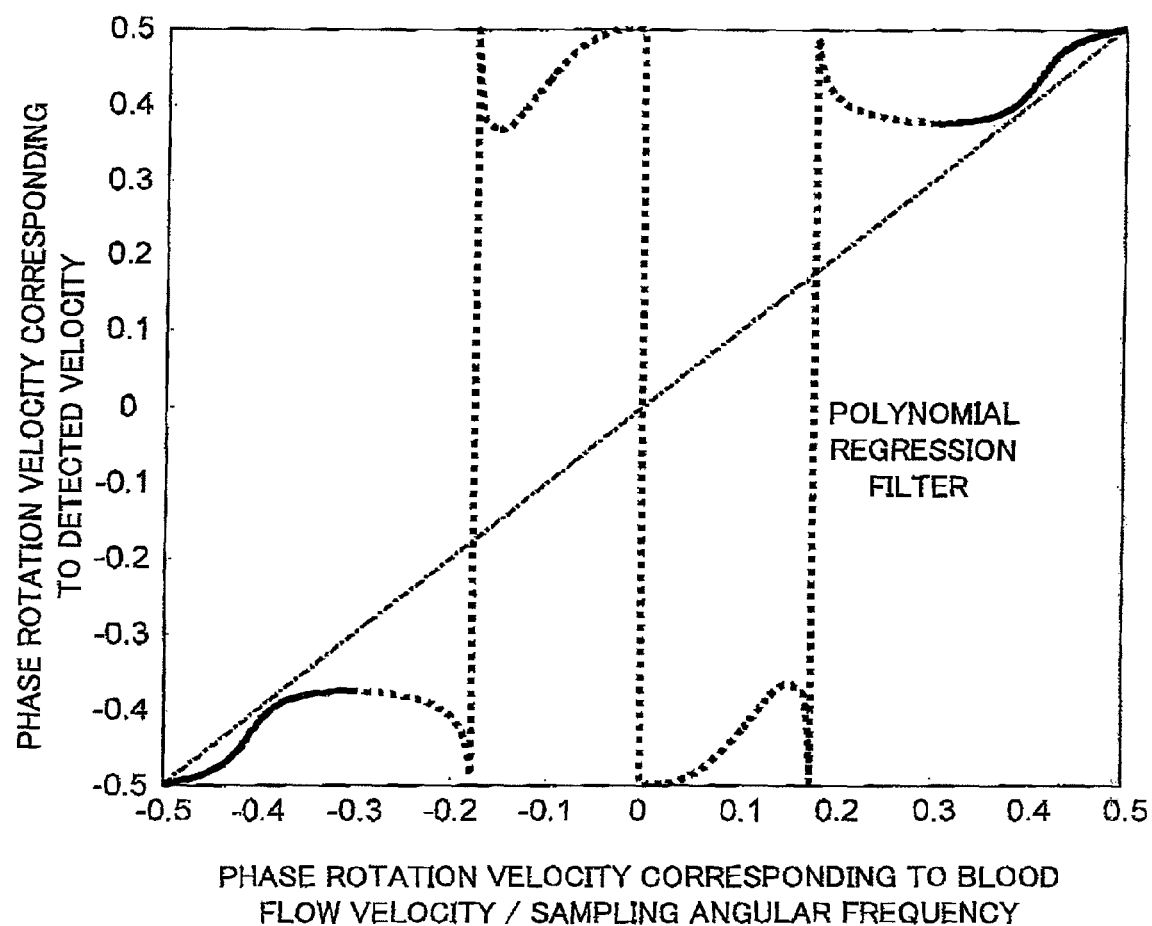
FIG. 33 shows an example of the velocity detection result obtained by using the polynomial regression filter.
Figure 34:
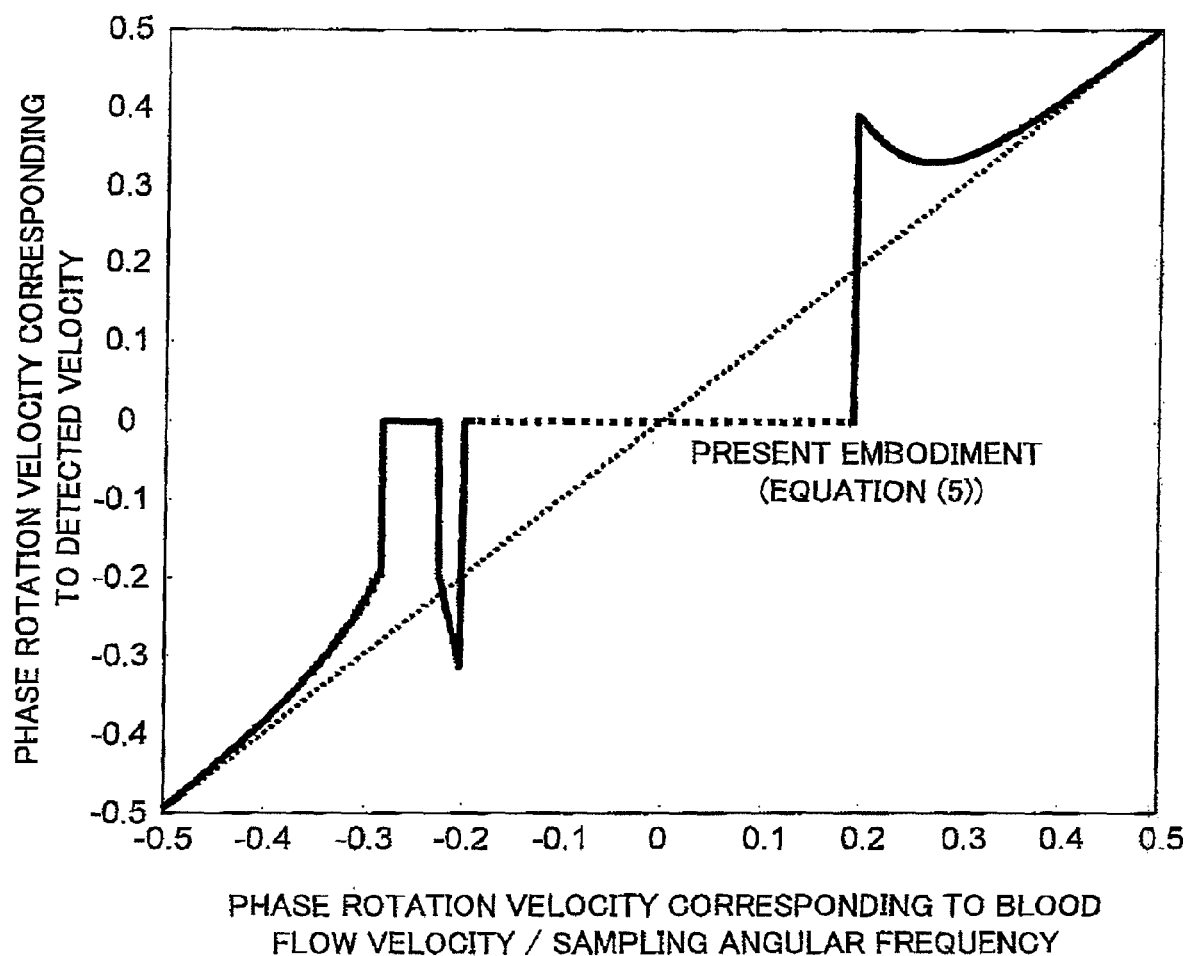
FIG. 34 is a flowchart showing an example a detection result obtained by using the Doppler velocity detection method of the present embodiment.
Figure 35:
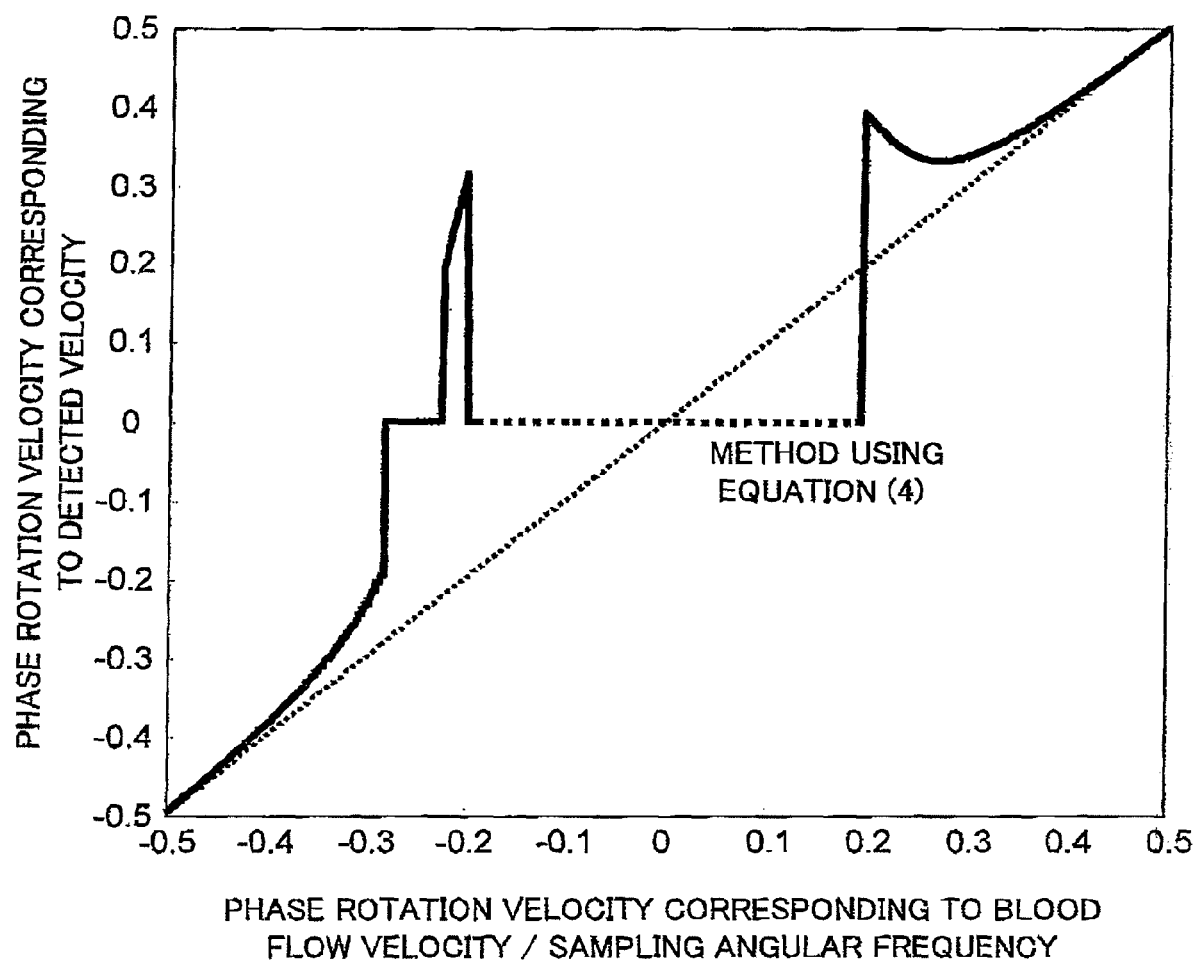
FIG. 35 is a flowchart showing another example the detection result obtained by using the Doppler velocity detection method of the present embodiment.
Figure 36:
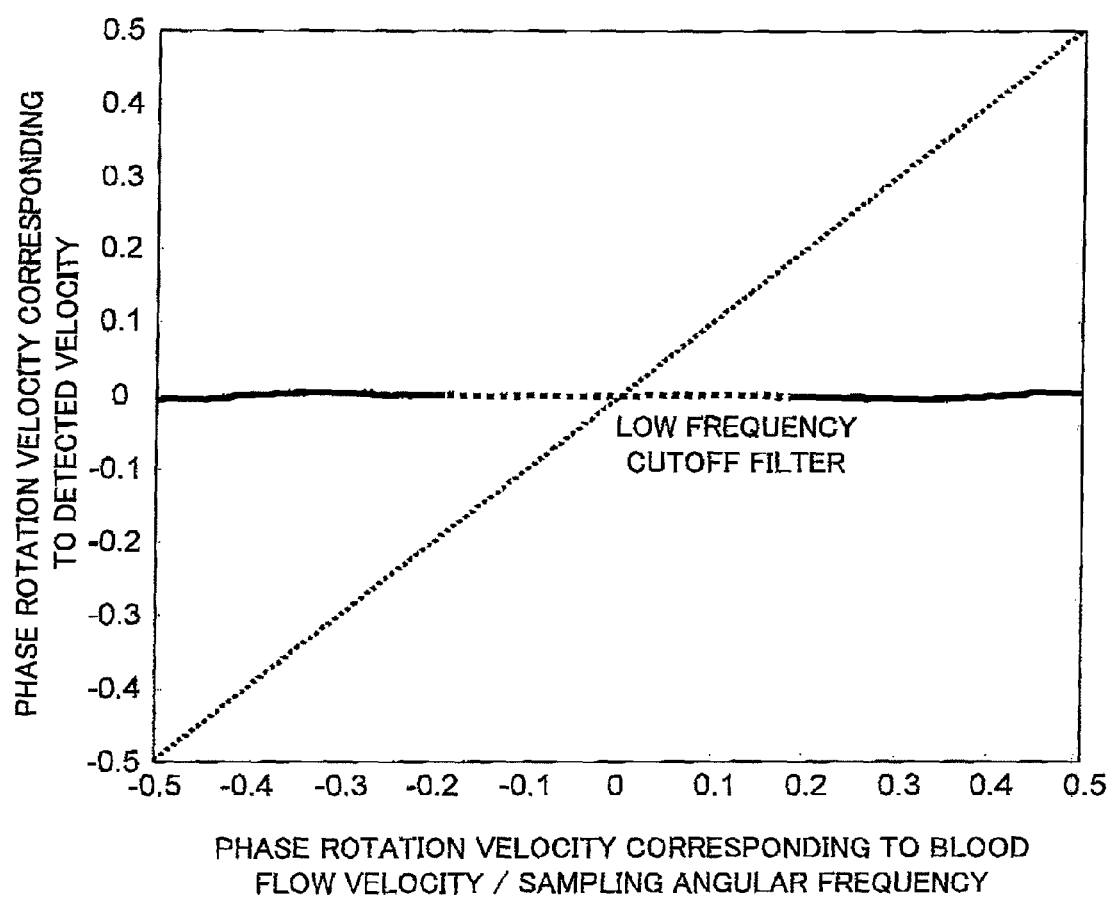
FIG. 36 shows an example of the velocity detection result obtained by using the conventional method.
Figure 37:
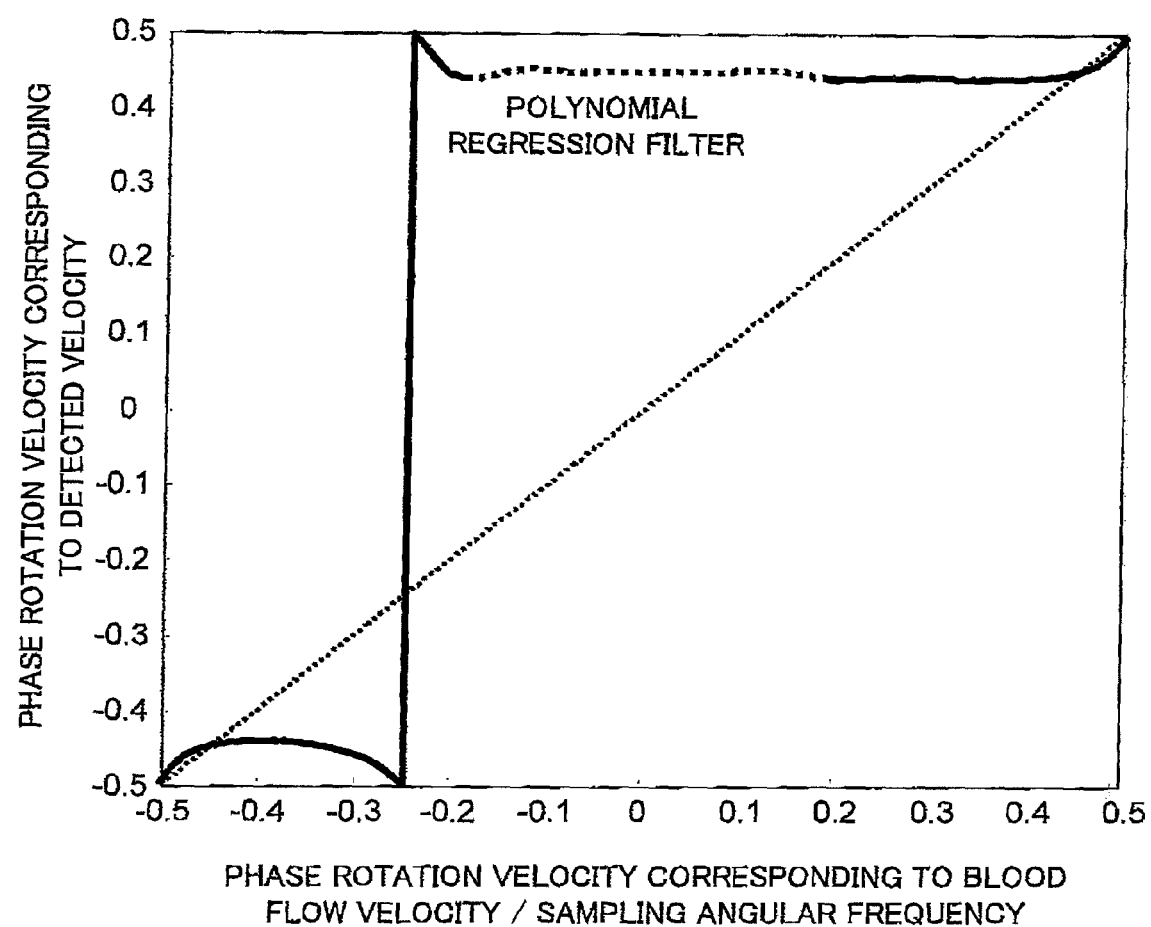
FIG. 37 shows an example of the velocity detection result obtained by using the polynomial regression filter.

Further, FIGS. 31 to 33 respectively show the velocity detection result obtained by using the method of the present embodiment, by using the method of the low frequency cutoff filter and by using the method of the polynomial regression filter, in the case where the final attainable velocity of the clutter reaches to 20% of the Nyquist limit velocity. If the clutter velocity reaches to such a high level, the velocity detection using the conventional method completely can not be performed. As to the method using the polynomial regression filter, the error becomes large within the effective velocity detecting range, and becomes particularly large when the blood flow velocity becomes lower than the effective velocity detecting range. In contrast, although the effective velocity detecting range becomes slightly narrower, the method of the present embodiment can not only provide substantially precise velocity detection result when the blood flow velocity is equal to or higher than 60% of the Nyquist limit velocity, but also unreservedly outputs a zero value when the blood flow velocity becomes lower than 60% of the Nyquist limit velocity.

Further, FIGS. 34 to 37 respectively show the velocity detection results obtained by using the method of the present embodiment that uses the equation (5), by using the method that uses the equation (4), by using the method of the low frequency cutoff filter and by using the method of the polynomial regression filter, in the case where the blood flow velocity itself has a random phase error corresponding to 8% of the Nyquist limit velocity. The final attainable velocity of the clutter was 10% of the Nyquist limit velocity. Since the blood flow velocity itself has a random phase error, the method of the present embodiment is about to become unreliable in the low and medium zone of the negative side, however the method using the equation (5) still can detect the velocity sign without failure, but the method using the equation (4), on the other hand, can not. This is because of the effect of using the equation (5) that is established to restrict the frequency sidelobe level. As to the method using the polynomial regression filter, it can not work any more in the low and medium zone of the negative side, and it can barely detect the velocity sign in the other velocity zone. Also, since the clutter velocity is high, the velocity detection using the conventional method completely can not be performed any more.

With the present embodiment, the blood flow can be drawn in distinction from the movement of an organ. To further make use of this character, in the ultrasonic diagnostic apparatus shown in FIG. 23, the clutter signal (namely the phase rotation velocity of the organ echo) detected by the phase rotation detector 13 is input into the scanning converter 19, so that the image showing the moving velocity of the organ or showing the distribution of spatial differential of the velocity and the blood flow image can be displayed in a manner in which the both images are superimposed or aligned. The usability of such a configuration is described below by taking an example of a liver tumor. The peripheral zone of the liver tumor is vascularized, and the movement of the blood flow of the peripheral zone of the liver tumor is different from that of the neighboring normal tissue of the liver. Further, since the peripheral zone of the liver tumor has different hardness compared to the neighboring normal tissue of the liver, the movement of the tissue of the peripheral zone of the liver tumor is different from that of the neighboring normal tissue of the liver. Thus, being able to display the variation of the organ moving velocity in accordance with the position in addition to the blood flow image means being able to provide an image very useful for liver tumor diagnosis.

Further, the velocity of the moving reflection object such as the blood flow in a living body can be precisely detected without being effected by the clutter echo signal whose amplitude is incomparably greater than that of the moving reflection object echo. Specifically, the blood flow having a velocity component toward the ultrasonic probe of 3 mm/s or higher can be drawn in real time in a case where the moving velocity of the organ toward the ultrasonic probe changes 1 mm/s. Thus, with the present embodiment, it becomes possible to provide an ultrasonic diagnostic apparatus having blood flow detecting/drawn function and capable of performing precise diagnosis. In other words, the apparatus which implements the present embodiment is very useful for the medical diagnosis, and the present embodiment has great significance for industries which support the medical diagnosis. Further, the method of the present embodiment can dramatically improve the detecting ability of pulse Doppler radar apparatuses or other pulse Doppler apparatuses for detecting moving reflecting objects, the pulse Doppler radar apparatuses including a weather radar that detects and draws the moving reflection objects such as nimbuses by transmitting/receiving electromagnetic waves, an aviation radar that detects flying objects, and a collision preventing radar that detects approaching objects. Thus, the present embodiment has great significance for industries and society.

[Modification]

The present invention is not limited to the aforesaid embodiment but should include various modifications such the following.

(1) Although the degree m of the coefficient having the maximum absolute value, among the complex expansion coefficients, is obtained, and the Doppler velocity is calculated from the ratio of the square sums of the expansion coefficients with the degree m as a boundary in the aforesaid embodiment, the Doppler velocity also can be calculated from the ratio of the square sums of the complex expansion coefficients.

(2) Although the aforesaid embodiment is applied to a diagnostic blood flow meter or a blood flow drawing apparatus which use ultrasonic wave to indicate a velocity distribution of the blood flow in the living body or a space distribution of the velocity, it also can be applied to pulse Doppler radar apparatuses such as a weather radar that detects and draws the moving reflection objects such as nimbuses by transmitting/receiving electromagnetic waves, an aviation radar that detects flying objects, and a collision preventing radar that detects approaching objects.

The invention claimed is:

1. A velocity measuring method for measuring a velocity of a moving reflection object constituting a velocity measuring object by using N time series signals formed by arranging echo signals of N pulse waves, which are sequentially transmitted toward the velocity measuring object at a predetermined time interval and are received as the echo signals, in order of the transmission time, the velocity measuring method comprising:
   an acquisition step of acquiring echo signals of the N pulse waves;
   an expanding step for expanding the N time series signals by using 0-th to (N−1)-th degree discrete Legendre function as a base;
   a complex expansion coefficient calculating step for calculating a 2n-th degree complex expansion coefficient by multiplying a linear combination of a (2n−1)-th degree expansion coefficient and a (2n+1)-th degree expansion coefficient by an imaginary unit and then linearly combining the result and a 2n-th degree expansion coefficient, and calculating a (2n+1)-th degree complex expansion coefficient by multiplying the (2n+1)-th degree expansion coefficient by an imaginary unit and then linearly combining the result, the 2n-th degree expansion coefficient and a (2n+2)-th degree expansion coefficient, wherein n is a natural number, the expansion coefficients are obtained by the expanding step; and the degree of the expansion coefficients is 1 or over and (N−1) or below;
   a degree determining step for determining a degree m of a coefficient having the maximum absolute value among the complex expansion coefficients; and
   a velocity signal calculating step for calculating a velocity of the moving reflection object as a signed velocity signal distinguishing its direction whether it is a transmitting direction of the pulse waves or an opposite direction from a ratio of square sums of the expansion coefficients or complex expansion coefficients corresponding to the degree m.

2. The velocity measuring method according to claim 1, wherein
   the expanding step is a step for multiplying a vector FF by a column vector Sd(n) whose elements are the time series signals, the vector FF being calculated by the following steps: a step of expressing a n-th degree discrete Legendre function as a row vector L(n), generating a N×N matrix LL by arranging the row vector in order of n =0, . . . , (N−1) in column-wise and transposing the N×N matrix LL to obtain a transposed matrix $^t$LL; a step of performing a multiplication of the transposed matrix $^t$LL and the N×N matrix LL, and calculating an inverse matrix $(LL\cdot{}^t LL)^{-1}$; and a step of performing a multiplication of the N×N matrix LL and the inverse matrix $(LL\cdot{}^t LL)^{-1}$.

3. The velocity measuring method according to claim 2, wherein
   the complex expansion coefficients are sequentially neglected in ascending order of the degree according to a variation of the magnitude of the echo of the stationary reflection object or drift degree of the stationary reflection object.

4. A velocity measuring method comprising:
   a step for determining whether the velocity measuring method according to claim 3 should be performed based on whether a detected velocity of zero is output when the velocity of the moving reflection object is lower than an effective velocity detecting range.

5. A velocity measuring device for measuring a velocity of a moving reflection object constituting a velocity measuring object by using N time series signals formed by arranging echo signals of N pulse waves, which are transmitted toward the velocity measuring object at a predetermined time interval and are received as the echo signals, in order of the transmission time, the velocity measuring device comprising:

an expanding means for expanding the N time series signals by using 0-th to (N−1)-th degree discrete Legendre function as a base;

a complex expansion coefficient calculating means for calculating a 2n-th degree complex expansion coefficient by multiplying a linear combination of a (2n−1)-th degree expansion coefficient and a (2n+1)-th degree expansion coefficient by an imaginary unit and then linearly combining the result and a 2n-th degree expansion coefficient, and calculating a (2n+1)-th degree complex expansion coefficient by multiplying the (2n+1)-th degree expansion coefficient by an imaginary unit and then linearly combining the result, the 2n-th degree expansion coefficient and a (2n+2)-th degree expansion coefficient, wherein n is a natural number, the expansion coefficients are obtained by the expanding means; and the degree of the expansion coefficients is 1 or over and (N−1) or below;

a degree determining means for determining a degree m of a coefficient having the maximum absolute value among the complex expansion coefficients; and a velocity signal calculating means for calculating a velocity of the moving reflection object as a signed velocity signal distinguishing its direction whether it is a transmitting direction of the pulse waves or an opposite direction from a ratio of square sums of the expansion coefficients or complex expansion coefficients corresponding to the degree m.

6. The velocity measuring device according to claim 5, wherein the expanding means is a means for multiplying a vector FF by a column vector Sd(n) whose elements are the time series signals, the vector FF being calculated by the following steps: a step of expressing a n-th degree discrete Legendre function as a row vector L(n), generating a N×N matrix LL by arranging the row vector in order of n=0, . . . , (N−1) in column-wise and transposing the N×N matrix LL to obtain a transposed matrix $^t$LL; a step of performing a multiplication of the transposed matrix $^t$LL and the N×N matrix LL, and calculating an inverse matrix $(LL\cdot{}^tLL)^{-1}$ of the product of the multiplication; and a step of performing a multiplication of the N×N matrix LL and the inverse matrix $(LL\cdot{}^tLL)^{-1}$.

7. The velocity measuring device according to claim 6, wherein the complex expansion coefficients are sequentially neglected in ascending order of the degree according to a variation of the magnitude of the echo of the stationary reflection object or drift degree of the stationary reflection object.

8. The velocity measuring device according to any one of claims 5 to 7, wherein the pulse wave is an ultrasonic wave; and
the moving reflection object is a blood flow.

9. The velocity measuring device according to any one of claims 5 to 7, wherein the pulse wave is an ultrasonic wave;
the velocity measuring object is a liver; and
the velocity measuring device further includes a display means for displaying the distribution of spatial differential of the velocity of the liver and displaying a blood flow image.

\* \* \* \* \*